(12) United States Patent
Kilpadi et al.

(10) Patent No.: US 6,656,496 B1
(45) Date of Patent: Dec. 2, 2003

(54) POROUS TISSUE SCAFFOLDING MATERIALS AND USES THEREOF

(75) Inventors: Deepak V. Kilpadi, Birmingham, AL (US); Dale S. Feldman, Birmingham, AL (US); Shu T. Huang, Birmingham, AL (US); Barbara Blum, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/914,802

(22) PCT Filed: Mar. 1, 2000

(86) PCT No.: PCT/US00/05401

§ 371 (c)(1),
(2), (4) Date: Sep. 4, 2001

(87) PCT Pub. No.: WO00/51538

PCT Pub. Date: Sep. 8, 2000

Related U.S. Application Data

(60) Provisional application No. 60/122,302, filed on Mar. 1, 1999.

(51) Int. Cl.[7] .............. A61F 13/00; A61F 2/00; A61F 2/44
(52) U.S. Cl. .......... 424/448; 424/449; 424/423; 424/422; 623/17.16
(58) Field of Search ............. 424/448, 449, 424/423, 422; 623/17.16

(56) References Cited

U.S. PATENT DOCUMENTS

| | | | |
|---|---|---|---|
| 5,092,841 A | 3/1992 | Spears | 604/96 |
| 5,199,951 A | 4/1993 | Spears | 604/96 |
| 5,207,670 A | 5/1993 | Sinofsky | 606/8 |
| 5,304,372 A | 4/1994 | Michalski et al. | 424/94.64 |
| 5,529,914 A | 6/1996 | Hubbell et al. | 435/182 |
| 5,540,677 A | 7/1996 | Sinofsky | 606/8 |
| 5,552,452 A | 9/1996 | Khadem et al. | 522/63 |
| 5,569,239 A | 10/1996 | Sinofsky | 606/8 |
| 5,583,114 A * | 12/1996 | Barrows et al. | 514/21 |
| 5,607,694 A | 3/1997 | Marx | 424/450 |
| 5,791,352 A * | 8/1998 | Reich et al. | 128/898 |
| 5,874,500 A * | 2/1999 | Rhee et al. | 525/54.1 |
| 5,885,829 A | 3/1999 | Mooney et al. | 435/325 |
| 5,886,026 A | 3/1999 | Hunter et al. | 514/449 |
| 6,054,122 A * | 4/2000 | MacPhee et al. | 424/94.4 |
| 6,056,970 A | 5/2000 | Greenawalt et al. | 424/426 |
| 6,428,576 B1 * | 8/2002 | Haldimann | 623/17.16 |

* cited by examiner

Primary Examiner—Thurman K. Page
Assistant Examiner—Isis Ghali
(74) Attorney, Agent, or Firm—Gifford, Krass, Groh, Sprinkle, Anderson & Citkowski, P.C.

(57) ABSTRACT

A biodegradable scaffold includes a protein, a cross-linking agent, 10 to 50 percent by volume porosity imparting polymeric beads and a modifying agent. A method for the use of the biodegradable scaffold is also provided.

16 Claims, 7 Drawing Sheets

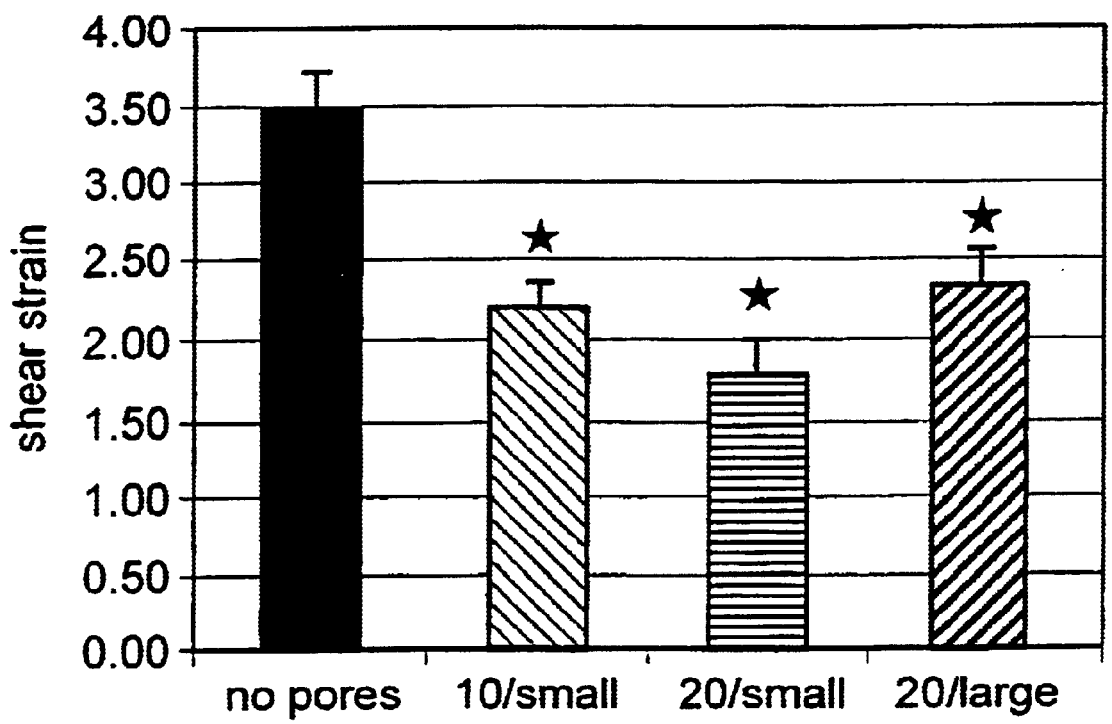

POROUS TISSUE SCAFFOLDING MATERIALS AND USES THEREOF

This application claims the benefit of Provisional Application No. 60/122,302, filed Mar. 1, 1999.

GRANT REFERENCE

This research was supported in part by CDC grant R49-CCR411774.

BACKGROUND OF THE INVENTION

1. Field of the Invention

The present invention relates to the fields of biomedical engineering and the chemistry of wound healing and biological glues. More specifically, the present invention relates to a novel porous tissue scaffoldings, which enhance wound healing and also serve as biological glues.

2. Description of the Prior Art

Skin injuries are a primary cause of death in North American for people between the ages of 1 and 44. Although different in etiology and prognosis, the treatment goal for all types of wounds is the same: skin regeneration. Two of the most common skin wounds are skin ulcers and burns. The most prevalent skin ulcers are pressure ulcers, diabetic ulcers, and venous statis ulcers.

There are various types of skin wounds. For example, pressure ulcers, caused by prolonged excessive pressure, and burns, caused by excessive heat, are significant problems in this society. Both heal in the clinical setting, once the causative agent is removed, although improving the speed and quality of healing is highly desirable.

Pressure ulcers are found in 20–30% of the approximately 200,000 spinal cord injury patients, 3–15% of nursing home residents or elderly patients, and in 3–11% of acute injury patients; for a total of approximately 800,000 patients per year. It is estimated that patients with pressure ulcers incur at least an additional $15,000/year in health care costs with estimates as high as $58,000. Enhancing the rate of regenerative healing would reduce the likelihood and effect of secondary complications.

It has been estimated that more than 500,000 persons are treated in a hospital emergency department each year due to thermal injury. Additionally, as many as 70,000 to 100,000 are hospitalized, and of these, 10,000 to 12,000 will die. Development of more active treatments can accelerate healing in these acute wounds as well as chronic non-healing; wounds and reduce morbidity and mortality associated with these skin wounds. Although little is known about the relative importance of and the relationships among the factors which enhance regeneration, it appears that the use of growth factors is one of the most powerful and direct methods presently, available to enhance and control wound healing. A degradable matrix used to deliver the growth factor, not only protects the growth factor which has a short in vivo half-life until release, but also serves as a scaffold for tissue formation.

Many investigators have examined ways to enhance and control healing. Healing is affected by altering the wound environment (oxygen, magnetic fields, stress, location, etc.) or wound biochemical activity (growth factors, growth hormone, and other biochemical agents). For skin wounds. rapid regeneration of connective tissue and the overlying epidermis is the goal. When a wound dressing or implant is used, wound healing can be altered by changing the implant configuration (pore size, porosity, fiber diameter etc.), the implant surface (composition, charge, surface energy, etc.), the implant biochemical activity (incorporation of growth factors or other biochemical factors), or the implant physical activity (degradation rate and drug delivery rate). Implants, used in the skin as tissue scaffolds, should be degradable to allow complete skin regeneration. When used beneath grafted skin, they should also allow rapid blood vessel infiltration and re-attachment (angiogenesis) between the graft and the underlying, tissue bed. In both cases, the interconnected porosity is critical for angiogenesis, since blood vessels require at least 40 mm pores to grow into a biomaterial. Additionally, an adhesive biodegradable matrix would help speed up the surgical procedure, of skin grafting, while enhancing juxtaposition between a skin graft and the underlying tissue bed.

One such biodegradable matrix is fibrin. Fibrin derived from blood has been used as a tissue adhesive. It is generally supplied as a two-component kit consisting of human-source fibrinogen/Factor XIII and bovine thrombin/$CaCl_2$. These fibrin sealants have been used since 1972 in Europe where a commercial version is presently available. No commercial product is available in the United States, and studies have been done using autologous or single donor preparation. Clinically, the fibrin matrix has been used as a hemostatic agent, for tissue anastomosis, as a fluid barrier, as a drug delivery vehicle, and as a tissue scaffold. Fibrin sealant used for skin grafting has been shown to increase attachment strength, to the wound bed, compared with staples, leading to less seroma formation and wound contraction.

Another biodegradable matrix suitable for use in wound healing and as a biological scaffold is modified polyethylene glycol (PEG) crosslinked albumin.

Using natural biomaterials, such as fibrin and albumin, delivery of a biochemical agent can be accomplished in a number of different ways. For example, the fibrin or PEG crosslinked albumin can be impregnated with the biochemical factor or agent; the agent can be attached to the polymer chain or it can be included through intra-fibril entrapment. Certain growth factors like FGF can bind to these polymers, like fibrin, Otherwise, the growth factors need to be attached through various linkages. When the growth factor is bound, it is released only when the fibrin or albumin degrades. Since the degradation is cellular, the growth factor release is controlled by the rate of phagocytic cellular infiltration and is thus under biofeedback control. Additionally, the degradation is at the wound edge and thus gives the appropriate gradient to stimulate further angiogenesis and tissue healing.

The use of a degradable matrix to deliver a biochemical agent, such as a growth factor, protects the growth factor until release, since it seems to have a short half-life in vivo even in the presence of heparin. This short half-life in vivo is potentially a problem for clinical studies using topical administration of growth factors, besides the inconvenience and added personnel expense.

Fibroblast growth factor (FGF), has been shown to induce angiogenesis. The mitogenic, chemotactic and differentiation properties of this growth factor suggests that it is involved in embryonic development and is probably a major trophic factor operating at all stages of embryogenesis. Unlike other growth factors such as platelet derived growth factor (PDGF), transforming growth factor, and epidermal growth factor (EGF), FGF can stimulate in vivo as well as in vitro proliferation of all cell types involved in wound healing. In, vitro studies have demonstrated that FGF inhibits contraction while enhancing wound healing. The inhibition of contraction may have therapeutic implications in the prevention of contracture scars. FGF has also been shown to increase graft survival by stimulation of epithelialization by cultured keratinocytes and vascularization in the wound bed in athymic mice.

Both basic FGF (FGF-2) and acidic FGF (FGF-1) are extremely angiogenic in vivo and mitogenic for fibroblasts in vitro. A preferential response by keratinocytes to FGF-1 in either the presence or absence of heparin, compared to FGF-2, has been reported. Stimulation of angiogenesis, granulation tissue formation and neo-epithelialization as well as increased wound strength, with increased cellularity and collagen deposition, without promoting contraction have been demonstrated in response to FGF-1, in vivo, in dermal wounds.

Clinical measures of wound healing include estimates of skin graft take, area healed, time to subjective healing, and length of hospital stay. Even the more quantitative measurement of change in surface area healed suffers from variability due to the effect of wound size on healing rate. The larger the wound, the more tissue that can be laid down in each time period, and the larger the change in volume or surface area. The optimal parameter to assess rate of healing should be independent of wound size. A measure that fits this description is the change in average wound diameter. It has been shown that the epidermal migration rate is relatively constant at approximately 1–2 mm/week.

Additionally, skin grafts secured with sutures or staples are commonly used in the treatment of patients with third degree burns. The associated potential for fluid collection between the wound surface and the grafted skin, which comprises the viability of the graft, may be minimized by attaching grafts using naturally occurring glues. Also, these glues provide a scaffold for tissue and can be impregnated with growth factors and antibiotics to enhance wound healing. In addition, the rate of degradation can often be controlled by biofeedback. Fibrin glue is a popular choice for applications of this nature and has recently been approved for hemostatic uses in the U.S. The current cost ($300/2 ml) has precluded the widespread use of this product in the U.S. Hence, applicants are examining other commercially viable alternatives. One such possibility is albumin glue, which is FDA approved, does not have the disease concerns associated with fibrin, and is considerably cheaper.

The prior art is deficient in the lack of effective means of facilitating the repair or regeneration of biological structures such as in the healing of wounds. The present invention fulfills this longstanding need and desire in the art.

SUMMARY OF THE PRESENT INVENTION

Therefore, it is an object of the present invention to design biodegradable scaffold or porous materials which are capable of locally delivering at least one agent including fibroblast growth factor (FGF-1). The present invention also provides a bioadhesive scaffold or porous material including albumin, a polyethylene crosslinking agent, and a modifying agent incorporated into the bioadhesive material.

Other and further aspects, features, and advantages of the present invention will be apparent from the following description of the presently preferred embodiments of the invention given for the purpose of disclosure.

BRIEF DESCRIPTION OF THE DRAWINGS

A better understanding of the present invention will be had upon reference to the following detailed description when read in conjunction with the accompanying drawing, and in which:

FIG. 10 is a graph illustrating the mean shear strain at ultimate strength wherein bars represent standard mean error (SEM) and * indicates significance (P<0.05) with respect to non-porous material.

DETAILED DESCRIPTION OF THE PRESENT INVENTION

Figure 1:
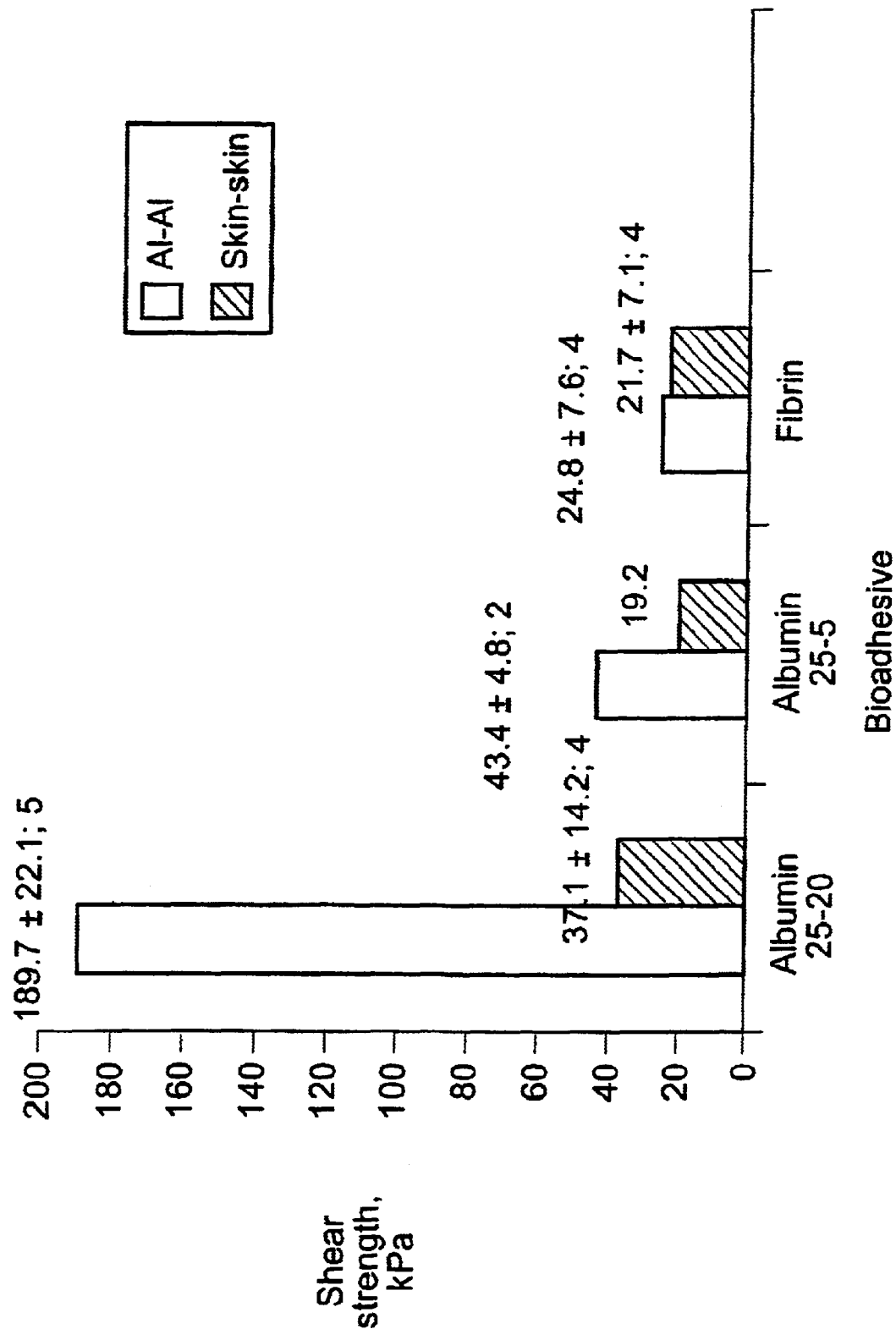
FIG. 1 illustrates the shear strength of PEG crosslinked albumin and fibrin.

In accordance with the present invention there is provided bioadhesive scaffold materials, which are biodegradable and serve as porous degradable tissue scaffolds and drug delivery mechanisms for the repair and/or regeneration of biological structures. The bioadhesive scaffolds in accordance with the present invention can include fibrin and modified-polyethylene glycol (PEG) crosslinked albumin.

These porous degradable tissue scaffold materials can be utilized as hemostatic agents, tissue adhesives, drug delivery matrices, tissue scaffolds, and combinations thereof in the areas of neurology (to reconnect nerves), orthopedics (for attachment of cartilage, bone, and implants), dentistry (for bone and implants), burns and trauma (for skin grafts), pressure ulcers, ophthalmology (corneal overlays), general surgery (replacement of surgical sutures), gastroenterology, and the filling of a fistula or defect in general, dental, and orthopedic surgery. The bioadhesive material can be utilized as a general tissue sealant to prevent leaks or as a bonding agent.

The present invention provides a bioadhesive scaffold composition which has high mechanical strength, flexibility, fast cure rate, and sufficient adhesion to bond and/or seal tissue in vivo.

The preferred scaffold materials for the present invention include serum albumin protein and fibrin.

The crosslinking agents can include any suitable crosslinking agent known to those skilled in the art. However, the preferred crosslinking agent for the present invention is polyethylene glycol (PEG) or modified polyethylene glycol such as polyethylene glycol succinimidyl propionate (PEG-SPA). The polyethylene glycol can also be used in bead form to make the matrix porous.

The components which make up the bioadhesive scaffold materials are preferably mixed together and immediately applied and/or used in the desired application. The fibrin is preferably present in a concentration of 1–60 mg/ml final concentration. The albumin is preferably present in an amount ranging from approximately 0.1% to 50% by concentration (0.01–0.50 g/ml). More preferably, the albumin is present in an amount of approximately 1.0% to 30% concentration and, most preferably, the albumin is present in an amount ranging from 10–30% concentration. The PEG can be used for three separate structural changes to the albumin or fibrin: to attach factors to the polymer (fibrinogen or albumin), to crosslink the polymer, or to be used as water soluble beads to create porosity. The PEG to attach factors can be used to get one to six attachment sites per molecule. For fibrinogen, one attachment per molecule is preferred. The PEG crosslinker is present in an amount ranging from approximately 0.1% to 30% by concentration. Preferably, the PEG is present in an amount ranging from between approximately 5% and 25% concentration. The PEG for imparting porosity uses 10–50% by volume of 10–500 $\mu$m (micron) PEG beads (5,000–2,000,000 MW). Preferably, the PEG beads are in the 10–20% by volume of 120–200 $\mu$m beads (20,000–100,000 MW). It should be noted, that the relative amounts of fibrinogen, albumin, crosslinking agent (PEG), and PEG beads may be varied in order to alter the properties of the bioadhesive scaffold material including the curing time and the viscosity. That is, the relative amounts of the components may be altered, for example, in order to tailor the bioadhesive material to a specific application or method of applying the bioadhesive material.

The bioadhesive scaffold materials can be applied by any suitable technique including the use of an applicator, injected via a syringe or sprayed.

As briefly discussed above, the bioactivity of the bioadhesive scaffold materials can be altered by the incorporation of factors or agents, such as pharmaceuticals, into the bioadhesive scaffold material which are subsequently released over time as the bioadhesive material degrades. Exemplary agents or factors include growth factors such as Fibroblast Growth Factor I (FGF-1), anti-inflammatory agents, antibiotic agents, and pore forming agents.

The following examples are given for the purpose of illustrating various embodiments of the invention and are not meant to limit the present invention in any fashion.

EXAMPLE 1

Manufacture of Porous Material

Pooled donor fibrinogen and bovine thrombin was obtained from the American Red Cross blood bank. The fibrinogen cryoprecipitate was re-suspended at 37° C. with 3.3 ml of ddH$_2$O to obtain a concentration of 120 mg/ml. The thrombin solution was prepared at 1000 units/ml in a 80 mM CaCl$_2$ dihydrate solution. The fibrinogen was mixed with thrombin in a 1:1 ratio, giving an ultimate fibrinogen concentration of 60 mg/ml.

Polyethylene glycol (PEG)(MW=20,000 Daltons) beads of 100–22 $\mu$m diameter (Shearwater Polymers, Inc. Huntsville, Ala.) were added to the thrombin. The 1.2 ml of PEG corresponded to a total of 12% by volume addition to the final fibrin clot. This volume was chosen because studies have indicated that 12% volume of the beads ensures interconnecting porosity, (Mikos et al., 1993).

EXAMPLE 2

In Vivo Testing

Five 6 mm diameter ulcers up to the depth of bare cartilage were created in each rabbit ear after routine surgical preparation, using a trephine. There were four rabbits in the study. There were two periods of study (four and eight days), with two rabbits in each study period. There were fifteen ulcers in each time period, five of which were treated with a porous fibrin scaffold, five with a non-porous fibrin scaffold and five were untreated to serve as controls.

All the ulcers were handled using sterile procedures to prevent infection. After the rabbits recovered from surgery, they were housed under veterinary supervision and returned to individual cages where they were checked and fed daily. Clinical evaluations were made daily and the ulcers were monitored. At the predetermined day, the rabbits from each time period were sacrificed by barbiturate overdose. The ulcer and surrounding tissues were removed. The specimens were then placed in an acid alcohol fixative for light microscope studies.

The implants were embedded in paraffin, sectioned, and stained. Hematoxyline and eosin staining was used for routine observation of cells and Masson's trichrome stain for measuring collagen formation. The stained tissue sections were evaluated by histomorphometrical methods to obtain the volume fractions of the various cellular and tissue components. This technique allows volume and other 3-D parameters to be obtained from 2-D measurement of the object. The volume percentage of cell types {macrophage (Mv), fibroblasts (Fv) and polymorphonuclear leukoctyes (Nv)}, tissue composition {apparent blood vessels (Bv) and collagen (Cv)}, and number of blood vessels (NB) per field were determined at the ulcer edge and the center of the ulcer. Mv, Nv, and Fv were determined using photographs of fields taken from the light microscope. Bv, NB and Cv were determined using an image analysis system (IBAS, Kontron Image Analysis Division, Munich, Germany). Because of possible shrinkage of blood vessels during the histological processing, the volume fraction of bloods vessels were categorized as "apparent volume fraction."

Data from four random fields (from at least two different sections) for each ulcer, both center and edge, were average to give one value per parameter for each ulcer. The epithelialization rate (ER) and the contraction rate (CR) of the healing ulcer was determined. Epithelialization rate was calculated by measuring the length of new epithelial tissue and dividing this value by the number of weeks in the time period (4/7 or 8/7), thus giving the value in mm/week. New epithelium is epidermal cells growing over the ulcer, which can be distinguished by the type of collagen and presence of hair follicles. Contraction rate was determined by measuring the original ulcer size, and subtracting that value from the diameter of the initial ulcer size (6 mm). The resulting value was also normalized by dividing by number of days in the time period, thus giving the value in mm/week. These data were then used to compare the three treatment groups. The critical factors were the extent of angiogenesis (NB, Bv), the fibroblastic (Fv) response and epithelial coverage. SAS version 5 (SAS Institute, Cary, N.C.) software program was used to perform analysis of variance and least square means, using the general linear model, to detect significant differences among the 6 groups. All tests were two tailed, with a level of significance of p <0.05.

Although the histomorphometric data at day four showed differences among the groups, the only statistically significant difference was between the control and the treatment groups was in Cv. The Cv for the porous fibrin treated group was about 80% higher than that of the control group at both the center and the edge of the ulcer. There were no statistically significant differences between the edge and the center of the ulcer for any of the parameters at this time period.

Several histomorphometric parameters, Nv, Mv, Fv, Cv and NB, showed significant differences between the treatment groups and the control on day eight. The Nv for both the center and edge of the ulcer in the non-porous treated group was highest among all three groups, but both treated groups were higher than the controls. The Nv for the control group was about 80% lower, and the Nv of the porous fibrin treated group was about 60% lower than that of the non-porous fibrin treated group at the center of the ulcer. At the edge of the ulcer, the Nv for the control group was about 82% lower, the Nv of the porous fibrin treated group was 73% lower than that of the non-porous fibrin treated ulcers. There were also significant differences between the center and edge of the ulcer in the porous fibrin treated groups. The Nv at the edge of the ulcer was about 51% higher than that seen at the center of the ulcer.

The Mv at the center of the ulcer for the control group was about 70% lower than that seen for the non porous scaffold treated ulcers. The Fv for the control ulcers at both the center and the edge of the ulcers was about 88% lower than that seen for the fibrin treated groups. The Cv for the control ulcers was about 110% higher than in the treatment groups at both the center and the edge of the ulcers. The NB for the porous fibrin treated ulcers was significantly higher at the center and at the edge of the ulcers than both the non-porous and the control groups. The NB per field for the porous scaffold was about 400% higher than control and 225% higher than the non-porous scaffold.

Between four and eight days, the fibrin treated groups showed a significant decrease in Cv and an increase in Nv and Fv. The control group, however, showed a significant increase in Cv at the end of day eight. In the porous fibrin treated group, the NB at the termination of the study was significantly higher than that seen at four days. The Mv at the edge of the ulcer also showed a significant increase at the end of the study. Epithelialization rate in all the groups was significantly higher at eight days compared to that at four days. Overall there were a few statistically significant differences in histomorphometric measurements between the ulcer edges and the ulcer center. These differences were seen only after eight days.

The rabbit ear ulcer model permits the study of wound healing without the confounding effects of contraction (Mustoe et al., 1991) and higher skin mobility normally seen in dorsal rabbit skin models (Pandit et al., 1994). The rabbit ear is an excellent model to study angiogenesis because it is relatively avascular.

The n value, which determines the sensitivity of the study, was carefully considered in the experimental design. For example, with the n value of 5, as used herein, the detectable difference for each parameter is approximately 1.5 times the standard deviation. With standard deviations averaging about 50% of the mean, changes in the mean of about 75% would be needed to detect significant differences. This difference is relevant to clinical significance. Although this design will not detect small differences in healing, it was selected on the basis of clinical significance. For example, the healing times for full-thickness burns and pressure ulcers would have to be significantly reduced to make a new treatment preferable over the standard skin grafting techniques. In the case of pressure ulcers, if healing rate could be cut in half, it would approximate the six weeks of hospital bed rest that normally follows skin graft surgery, rather than the usual three to six months for conservative treatment.

Little contraction was seen; thus, overall healing can be approximated by the percent of the ulcer covered by epidermal cells. Al the end of four days, the ulcers were about 20–30% epithelialized, and 90–95% epithelialized at the end of eight days.

The histomorphometric parameters used were indicators of the healing response. To decide upon the optimal system to be used in clinical trials, it was necessary to prioritize the individual histomorphometric parameters. The overall healing rate, approximated by the epithelialization rate, is the most important clinical measure. Therefore, this parameter was given the highest priority. Because of the importance of angiogenesis (Bv, NB) and fibroblasts (Fv and Cv) in the scaffolding effect of the matrix, these parameters were given the next priority. The time course of the inflammatory response (Mv and Nv) is also critical in determination of the optimal system.

This wound healing model has an extremely low contraction rate. In comparison, in a full-thickness dorsal defect model, wound closure during the first week was predominantly by contraction (CR—5.0 mm/wk) as opposed to epithelialization (ER—1.2 mm/wk), giving a CR/ER ratio of about 4:1. In the present invention, this ratio was approximately reversed with a 1:6 ratio at day four and a 1:4 at day eight for the control ulcers.

As increase in NB at both the ulcer center and edge by day eight indicated a higher angiogenic response in the porous scaffold treated ulcers. NB in three dimensions, based on histomorphometric principles, gives length per unit volume of blood vessels. Although not statistically different ($p=0.06$), the Bv for the porous scaffold at day eight was about 140% higher than the control at the center of the ulcer. The relatively high standard deviation for this measure (about 75% of the mean of the porous scaffold) made a difference in means of this magnitude too low to be detected in this design. The use of a higher n value or a one-tailed test in the original design would have made this difference statistically significant. No significant differences in angiogenic response was observed at day four. The enhancing effect of the scaffold appears to occur after the ulcer is about 30% healed.

A higher fibroblastic (Fv) reaction, as seen in both the fibrin scaffold treated groups, gave an indication of the amount and rate of collagen that could be produced and the quality of the ulcer. The Cv, however, which indicates collagen density, was higher for the porous system at day four but highest for the control at day eight. Both collagen density and healed ulcer volume would be needed to determine the total amount of collagen produced. The higher Nv and Mv reaction, when healing was nearly complete, indicated an enhanced inflammatory reaction for the fibrin scaffolds.

These results indicate that the healing response was modified by a fibrin scaffold. Both porous and non-porous fibrin scaffolds initiated a higher fibroblastic response, with the porous fibrin scaffolds initiating the highest angiogenic and fibroblastic response. A higher inflammatory reaction was also seen in the non-porous fibrin scaffold compared to the porous scaffold.

That a 100–200 μm degradable porous system leads to a significant increase in the angiogenic and fibroblastic response with a corresponding decrease in healing time as compared to untreated ulcers or non-porous systems was partially shown. The increase in angiogenesis and Fv did not correspond to an increase in epithelialization rate. Modifications to the system to increase the epithelialization rate would include optimization of the implant's scaffolding ability, both its configuration and bioactivity. This would include optimization of the implant porosity or other aspects of configuration to achieve significant enhancement of regenerative skin healing. Addition of biochemical factors (e.g., growth factors), alteration in the wound environment by changing the oxygen gradient and electromagnetic fields also are important in the modulation of epithelialization rate.

EXAMPLE 3

In Vivo Dose Response of Acidic Fibroblast Growth Factor Delivered Through a Porous Fibrin Scaffold on Wound Healing In order to enhance the scaffolding of a biomaterial both the bioactivity and configuration of the implant was examined. Parameters of bioactivity include rate of implant degradation as well as the use of incorporated biochemical factors such as growth factors. Parameters of implant configuration includes both surface roughness and porosity. A porous fibrin scaffold with a pore size of 100–200 μm initiated an enhanced fibroblastic and angiogenic response over the control ulcers.

EXAMPLE 4

Growth Factor Manufacture and In Vivo Dose Response

FGF-1 was expressed in Escherichia coli under the control of trp-lac promoter. Synthetic DNA fragments encoding the entire frame of human Fibroblast Growth Factor-1 and its $NH_2$-terminal truncated form were constructed and then expressed in E. coli.

The growth factor was added to fibrinogen prior to mixing, at the appropriate concentrations. The amount of FGF-1 added was equal to the amount desired to be released over a one week interval. For example, if it was desired to release 10 mg/ml PGF-1 to the ulcer each day for seven days; 70 mg (10×7) of FGF-1 was incorporated into the fibrin clot the size of the ulcer (6 mm or approximately 28.3 $mm^2$) Based on preliminary studies, approximately 0.14 ml would produce a clot to cover this size. Therefore, the concentration would be 2.47 $mg/mm^2$ (70 $mg/28.3 mm^2$) or 500 mg/ml (70 mg/0.14 ml) of fibrongen solution.

EXAMPLE 5

In Vivo Testing of Growth Factors

Five 6 mm diameter ulcers up to the depth of bare cartilage using a trephine were created on each rabbit ear after routine surgical preparation. A control ulcer with no growth factor, treatment along with four different combinations of the growth were tested. The growth factor was added in the following concentrations: 0.8, 8, 80 and 800 mg/ml. There were six rabbits in the study in this two period study (four and eight days) with three rabbits in each period of study. In each ear there were four ulcers and a control ulcer. Hence, there were five of each type of treatment per time period. Each ulcer was covered by a conventional "Opsite" (Smith & Nephew, Inc., Massillon, Ohio) wound dressing. Since it is expected that the growth factor will accelerate the growth rate, four and eight day tests were performed, less than the ten days required for complete healing of control wounds in earlier studies. The ulcers were handled using sterile procedures as described above.

EXAMPLE 6

Necropsy

At the predetermined termination day, the rabbits from each time period were sacrificed using barbiturates. The ulcers were removed and were placed in an acid alcohol fixative for light microscope studies. The implants were embedded in paraffin, sectioned, and then stained. Hematoxylin and eosin, for routine observation of cells, and Masson's trichrome, for collagen were used. To obtain the volume fractions of the various cellular and tissue components, the stained tissue sections were then evaluated using histomorphometry. This technique allows volume and other 3-D parameters to be obtained from 2-D measurements of the object. The volume percent of cell types {macrophage, fibroblasts and neutrophils} and tissue composition {volume fraction of blood vessels} were determined at the wound edge and the center of the wound. In addition, the number of blood vessels, epithelialization rate and the contraction rate of the healing ulcer was quantified. Mv, Nv, and Fv were determined using photographs of fields taken from a light microscope. Bv and NB were determined using an image analysis system (BAS, Kontron Image Analysis Division, Munich, Germany). Because of possible shrinkage of blood vessels were categorized as "apparent volume fraction". Data from four random fields (from at least two different sections) for each wound were averaged to give one value per parameter for each wound. In addition, epithelialization rate and contraction rate of the healing ulcer were quantified.

Epithelialization rate was determined by measuring the length of new epithelial tissue and dividing this value by the number of weeks in the time period (4/7 or 8/7); thus giving the value in mm/week. New epithelium is epidermal cells growing over the wound which can be distinguished by the type of collagen and presence of hair follicles. Contraction rate was determined by measuring the original wound size; and subtracting that value from 6 mm (the diameter of the initial ulcer size). The resulting value was normalized by dividing it by number of days in the time period; thus giving the value in mm/week. This data was analyzed to determine the best FGF1 concentration. The critical factors were the extent of angiogenesis (NB, Bv), the fibroblastic (Fv) response and epithelial (epithelialization rate).

EXAMPLE 7

Volume Fraction of Neutrophils (Nv)

At day four, the Nv at the center of the wound was significantly lower in the control wounds than all the treatment groups. Nv at the edge of the wound was, however, also lower than all the treatment groups except for 0.8 mg dose. There were no significant differences seen after the 8th day among any of the treatment groups. The Nv on day eight in the control group was about 200% higher than that seen on day four. Although there were differences seen between the two time periods in the other treatment groups, none of these were statistically significant.

EXAMPLE 8

Volume Fraction of Macrophages (Mv)

Mv, at the edge of the wound, in the control group after the four day treatment period was significantly higher than the treatment groups. Similar results were observed at the center of the wound with the exception of Mv for the 80 mg dose. At eight days no significant differences were observed between the treated groups and the controls. However, Mv for the 0.8 mg dose was about 110% higher than that seen for the 800 mg dose. The Mv on day four in the control group was about 75% higher than that seen on day eight. Although there were differences seen between the two time periods in the other treatment groups, one of these were statistically significant.

EXAMPLE 9

Volume Fraction of Fibroblasts (Fv)

For FV, there were no significant differences seen at the center of the wound at the end of four days, except in 8 mg where the Fv was about 60% lower than the control. The Fv at the center of the wound in the 8 mg treated groups however, was significantly higher than all the groups at the end of the eight day period. On day eight, 8 mg dose showed about a 310% increase in Fv at the center of the ulcer than that seen on day four and a 70% increase compared to the edge of the ulcer on day eight. Although there were differences seen between the two time periods in the other treatment groups, none of these were statistically significant.

EXAMPLE 10

Volume Fraction of Blood Vessels (Bv)

With respect to Bv, the control wound showed a lower response compared to the all the growth factor-treated groups on day four. The only significant differences were seen at the 8 mg and 0.8 mg dose. Among the growth factor treated wounds, the 8 mg treated defects showed a significantly higher Bv compared to all the other doses with the exception of 0.8 mg. There was no significant difference between these two doses although higher volume fraction of blood vessels were seen in the 8 mg treated defects. On day four, the 8 mg dose showed about a 200% increase in Bv at the center of the ulcer than as on day eight and a 120% increase than at the edge of the ulcer on day four. Also on day four, a 0.8 mg dose the Bv at the center of the wound showed a 160% increase than that seen on day eight.

EXAMPLE 11

Number of Blood Vessels (NB)

Significant differences were seen in the NB between the two time periods in the control ulcer at the edge of the wound. NB at the edge of the control wound at day eight was about 360% higher than that seen on day four. NB in the control group at the center of the wound was lower than all the growth factor doses. However, only the 80 mg and the 0.8 mg dose were significantly higher than the control. Similar results were seen at the edge of the wound with 0.8 mg dose being significantly higher than the control. Although there were differences seen between the two time periods in the other treatment groups, none of these were statistically significant.

EXAMPLE 12

Epithelialization Rate (ER)

Epithelialization rate in all the growth factor treated ulcers was significantly higher than that seen in the controls at the end of day four. The epithelialization rate in the FGF-1 treated ulcers were about 200% higher than that seen in the control. Epithelialization rate at the eight day time period in all the treatment groups with the exception of 80 mg and 0.8 mg were significantly higher than that seen on day four. No other significant differences were seen in the contraction rate among the treatment groups.

The present invention demonstrates the effective dosing regimen of FGF-1 through a porous fibrin carrier vehicle. Histomorphometric parameters were used as an indication of the healing response. It was necessary to prioritize the individuals parameters to determine the effective dosing regimen of FGF-1 to be used in clinical trials. The epithelialization rate, which approximates the overall clinical healing rate, was given the highest priority. Since the amount of angiogenesis (Bv, NB) and the fibroblastic response (Fv) play an important role in the quality of healing, these parameters were next in priority. The time course of the inflammatory response (Mv and Nv) is also important in the determination of the optimal dose of FGF-1.

Epithelialization rate was significantly enhanced by the growth factor treatments; indicating a faster closure of the wound by growth factor treatments at the four day period. This enhanced epithelialization rate response illustrates the faster rate of closure in the wound by growth factor treatments, at least in the early stages of healing (up to 30% re-epithelialization). Angiogenesis was markedly higher in the initial phase in the growth factor treated groups. This angiogenic response was not statistically different between the treatments and the control at day eight. This implies that FGF-1 is angiogenic and triggers the formation of blood vessels earlier in the treated wounds.

Increasing the rate of angiogenesis in the wound center implies that the rate of wound healing will be enhanced. Once the vessels infiltrate the center of the wound, which is normally low in oxygen, resident fibroblasts will produce more collagen and the epidermal repair rate should increase. Since blood vessels are responsible for transport of nutrients, immunoglobulin and white blood cells in the wound bed, resistance to infection is also increased by the enhanced angiogenic response.

A higher Fv in the 8 mg dose was seen at the wound center after eight days; although the same dose showed a significantly lower Fv than the other groups at day four. The higher Fv at eight days is likely to indicate an increase in the amount and rate of collagen production leading to an increase in overall wound strength. Also a good indication of the healing response is the inflammatory response (Nv & Mv). An initial high response in the growth factor treatments compared to the control indicated an initiation of an early inflammatory phase compared to the control ulcers.

In general, the growth factor treatments affected the healing response exhibiting a dose dependent behavior The addition of FGF-1 led to an increase in the angiogenic and fibroblastic response as well as an increase in the epithelialization rate. Based on the prioritized parameters, the preferred dose was 8 mg. This dose initiated a high epithelialization rate, fibroblastic and angiogenic response and was the lowest dose to initiate these responses. In order to compare the results to the topical regimes used in previous studies, it is necessary to determine the release kinetics of this system. Since FGF-1 has a short in vivo half life, the use of the scaffold serves to protect it until it is released. Therefore, this fibrin matrix serves as a controlled release drug delivery system, while providing an adherent tissue scaffold during healing.

EXAMPLE 13

Delivery of Rate of FGF-1 Through a Porous Fibrin Scaffold in a Full Thickness Defect in a Rabbit Model Controlled delivery refers specifically to the precise control of the rate by which a particular drug is released from a system without the need of frequent or repeated administration. Drug release rate, that is constant, over a fixed prolonged period of time follows zero order kinetics in which the rate is not affected by concentration. Biodegradable polymer matrices offer a major advantage in their use in the improvement in the design of controlled release devices for implantation as they may degrade in vitro to non-toxic products which are readily eliminated in the body. The advantage of controlled delivery in wound healing applications is to reduce problems in patient compliance and reduce costs of wound management while enhancing the rate of healing by delivery of bioactive factors. Controlled delivery also reduces the exposure of the patient to excessive dose of the drug required at the targeted site.

Acidic fibroblast growth factor has been demonstrated to modulate the healing response. A dose dependent behavior with the concentration of the growth factor has been observed. The different dose responses indicate that there is a release of FGF-1 in the wound from the fibrin scaffold. A dose of 8 mg/ml enhances an angiogenic and fibroblastic response. This dose was preferred because it was the lowest dose which initiated the best response. FGF-1 is released when fibrin is enzymatically degraded.

EXAMPLE 14

Lodination of FGF-1

Pooled donor fibrinogen and bovine thrombin were prepared as described above. Polyethylene glycol beads and FGF-1 were prepared as described above. FGF-1 was iodinated by the IODO-GEN method as described by Neufeld with some minor modification (Neufeld et al., 1980). IODO-GEN (Pierce, Rockford, Ill.) was dissolved in $CH_2Cl_2$ to a concentration of 5 mg/15 ml. 5 mg/15 ml of this solution was added to a 1.5 ml polypropylene tube and evaporated to dryness under a stream of nitrogen with FGF-1 (10 mg in 4.13 ml of 20 mM Tris-HCl, pH 7.5, 1 mM EDTA and 1.5 M NaCl) together with 100 ml of 0.2 M Sodium Phosphate (pH 7.6). The reaction was started by the addition of 1 mCi (1 Ci=37 GBq) IODO-GEN. After ten minutes at room temperature, the reaction was stopped by the addition of 60 ml of 0.1% sodium metabisulfite and 30 ml of 0.1 mM KCl. The reaction mixture was then poured on to a Sephadex G-25 column (PD-10 Pharmacia, Piscataway, NJ 08855-1327) for separation (Rizzino et al., 1988). The reaction tube rinsed with a equilibration buffer (10 mM HEPES, from a 1.5 M stock solution, pH 7.4), 0.3 M NaCl, 0.1% BSA and the rinse and was again loaded onto a Sephadex G-25 column. The labeled FGF-1 was eluted from the column with 10 mM HEPES buffer (pH 7.4, 0.3 M NaCl). The radiolabeled I-125-FGF-1 peak (from the Sephadex G-25 column) was then loaded on the heparin-sepharose CL-6B column (Pharmacia LKB, Uppsala, Sweden) for further purification. The labeled I-251-FGF-1 was recycled ten times over the column to ensure maximal binding. The heparin-Sepharose column was then washed with approximately 20 ml of 20 mM Tris HCl (pH 7.5, 1 mM EDTA (TE)) buffer, until low counts eluted from the column. The column was then washed with a 0.5M NaCl buffer in TE. I-125-FGF-1 was eluted from the column with elution buffer 2M NaCl in TE. The purification was affinity chromatography was 31.5%. The specific activity of the I125-FGF-1 was 31.5 mCi/mg. 350 mg FGF-1 was added to the I-125-FGF-1 solution and was mixed together for animal experimentation.

EXAMPLE 15

Surgery

The rabbits were shaved and a depilatory agent was applied a day before surgery to ensure adhesion of the dressings. Four 3×3 cm full-thickness defects down to the panniculus camosus muscle were created on the dorsum of each of five white New Zealand rabbits. There were five periods of study (1,2,5,8 and 16 days) with one rabbit per time period. This experimental design gave a n value of four per time period. The full-thickness defects on the dorsum of the rabbit were covered with the fibrin scaffold containing I-125 labeled FGF-1. The growth factor was added to fibrinogen prior to mixing, at the concentration of 8 mg/ml (Smith & Nephew, Inc., Massillon, Ohio) wound dressing. A transparent polyurethane, water vapor permeable, oxygen permeable, dressing (Opsite) was placed on these scaffolds. Dressings were secured with surgical tape around, the perimeter. A cotton orthopedic stockinette, cut to fit, was placed around the animal along with a torso sling suit (Alice King Chatham, Hawthorne, Calif.).

EXAMPLE 16

Necropsy

At the time of necropsy, the animals were euthanized. The fibrin film, the dressing and the wound site were retrieved at the pre-determined time period to assess release kinetics. Radioactivity was measured using a Picker Spectroscaler IIIA Gamma Counter (Picker X-ray Corporation, Cleveland, Ohio). Three readings of each of the four samples per time period were averaged. This radioactivity in the fibrin scaffold was used to determine the release rate of FGF-1. The radioactivity in the wound tissue and the wound dressing were also used to assess the growth factor distribution over time. A control in vitro reading of FGF-1 in a fibrin scaffold was taken to determine the initial amount of radioactivity present. A control wound at time zero was also made during necropsy and the fibrin scaffold containing FGF-1 was placed on the wound. In this case, after in situ polymerization the fibrin scaffold was immediately retrieved to determine the amount of FGF-1 present in the fibrin clot after implantation.

A wound model was selected by size and depth to take at least three weeks to heal. Full thickness skin defects in the rabbit model were used to simulate the initial phase of healing of skin wounds such as pressure ulcers and burns. A wound down to the level of the panniculus carnosus, was chosen to simulate human skin; since skin mobility is reduced due to the attachment to the muscle layer.

It was anticipated that the release rate of FGF-1 would be tied to the degradation of fibrin. Therefore, the amount of FGF-1 added was equal to the amount desired to be released over a one week interval. Incorporating FGF-1 in the fibrin scaffold during the clotting process is similar to intrafibrillar entrapment. It was also postulated that this release would occur only when cellular infilteration had taken place thus making it a biofeedback mechanism. Since, FGF-1 has a short in vivo half life, the use of a fibrin scaffold serves to protect is until it is released, thereby serving as a controlled release drug delivery system, while providing an adherent tissue scaffold during healing.

An immediate release of about 35% of the total amount of FGF-1 was seen. This loss could be attributed to immediate absorption of FGF-1 during in situ polymerization of fibrin. Hence, all of the release cannot be attributed to degradation of fibrin. On day one there was a release of up to 65% of the initial amount. This release could be accounted to diffusion of unbound FGF-1, and partly by enzymatic degradation of the porous fibrin scaffold by invading inflammatory cells. Thereafter, a sustained controlled release was seen in the subsequent time periods. This sustained release can only be attributed to enzymatic degradation of the scaffold. Degradation of the scaffold also proceeds in a controlled manner because of the type of cells present in the different phases of healing. It appears that this scaffold degrades completely between day eight and day sixteen approximating the time for these wounds to heal in this system. Hence, the initial release is diffusion controlled and the later release (after day one) is degradation controlled. The amount of FGF-1 released per day showed similar trends. An initial high release followed by constant release was seen. Thus, the porous fibrin scaffold served as an excellent vehicle for this growth factor.

EXAMPLE 17

Use of Acidic Fibroblast Growth Factor (FGF-1) Delivered Through a Porous Fibrin Scaffold to Enhance Meshed Skin Graft Healing Surgeons attempt to re-establish homeostasis in burn patients through meshed autologous skin grafts. Because these grafts contain no anatomical continuity with the donor site, the take of these grafts depends on rapid establishment of a functional circulation and adherence to the wound bed. Fibrin, the native adhesive in wounds, also acts as a scaffold for subsequent repair processes. Porous fibrin matrices have previously been shown to increase both the angiogenic and fibroblastic response. Additionally, fibrin matrices have been used as drug delivery devices, acidic fibroblast growth factor (FGF-1) has been incorporated into this degradable fibrin scaffold.

For this study, an initial fibrinogen concentration of 60 mg/mL was added to thrombin in a 1:1 ratio giving an ultimate concentration of 38 mg/ml. Water-soluble poly (ethylene oxide) (PEO) beads (17–24 microns in diameter, $2 \times 10^6$ MW) were added to the clot at 25% by volume to make the porous matrices. FGF-1 was used at a concentration of 10 mg/mL.

Five 0.75×0.75 inch full-thickness defects were created on the dorsum of each of twelve white New Zealand rabbits: five rabbits in each of two time periods (three and ten days). Skin harvested by dermatome was meshed (3:1) and cut to fit with the full-thickness wounds and attached via a fibrin scaffold, a porous fibrin scaffold, a porous fibrin/FGF-1 scaffold, or 4-0 prolene sutures. Fibrin was used at 39.5 mg/ml. Fibrin/FGF-1 was used at 38.5 mg/ml and 10 micrograms/ml, respectively. The concentration for porous fibrin was 35.8 mg/ml while the concentration of porous fibrin/FGF-1 was 34.7 mg/ml and 9 micrograms/ml, respectively. The wounds were covered with Tegaderm and the animals were sacrificed at three and ten days.

Upon sacrifice, the volume percent of cell types and tissue composition was determined. The healing rate, or the distance the wound margin moves, was calculated and is representative of the amount of new granulation tissue formed. For grafts, the muscle was excised to assay for newly formed tissue at a strain rate of 0.2 inches per minute. The fibrin tissue adhesive testing included porcine skin (0.01 inches thick). The volume of glue/area skin was similar to that used in vivo. The strain rate used was 2.0 inches per minute.

Over half of the porous fibrin grafts did not adhere. The sutured grafts showed a stiffer modular when compared with other treatments. The non-porous fibrin glue showed higher strength that the porous fibrin glue at five and forty-five minutes. The fibrin/FGF-1 treatment resulted in a low modulus at three days.

The porous fibrin matrix served not only to adhere the graft better but also to speed the healing rate versus the control. A relatively constant rate of FGF-1 release was observed and an increased angiogenic response was found when compared to the control.

EXAMPLE 18

Comparison of Shear Strength of Fibrin and Albumin Glues

The shear strengths of human abdominal skin adhered by either fibrin (1:1 ratio of fibrinogen to thrombin) or albumin, stabilized by cross-linking with polyethylene glycol (PEG), (25% albumin-5% PEG or 25% albumin-20% PEG) glue were compared. The fibrin had a shear strength of 6.2 kPa, the 25-5 albumin about 9 kPa (about 1.5 times the fibrin value), and the 25–20 albumin glue appears to have a shear strength of about 31 kPa (about 5 times the fibrin shear strength). Thus, albumin glue appears to have a substantially higher shear strength than fibrin when used as an adhesive for skin grafts.

EXAMPLE 19

Comparison of Albumin and Fibrin Glues f6r Use With Metallic Implants

Bone loading stimulates the rate of bone integration at optimal levels but can compromise bone stability, at higher loads. Dental implants are typically left unloaded for up to six months to minimize micromotion and to allow for bone integration and long term success. In addition, fixation of a percutaneous device is an important factor in preventing non-epidermal as well as epidermal failure. Fixation of dental implants helps prevent failure; allowing a tight seal at the gingival-implant interface minimizes micromotion as well as the risk of infection caused by breakdown at the implant surface.

The potential of using bioadhesives to reduce the time when an implant is unloaded, without compromising implant stability was examined. These bioadhesives also have the potential to serve as degradable scaffolds to further enhance tissue integration.

The adhesive shear strength of these bioadhesives is critical for both load transfer and implant stability. As an initial investigation, the adhesive shear strengths of fibrin and albumin glues were tested for both metal-metal and skin-skin cases.

Fibrin glue was made from a 1:1 ratio of fibrinogen (7000–9000 mg/dl) to thrombin (500 units/ml), buffered in 40 mM $CaCl_2$. Albumin glue consisted of 25% albumin—20% polyethylene glycol (PEG) or 25% albumin—5% PEG. Curing time after application was one hour for all systems.

For the skin-skin tests, the epidermal surface of human skin was adhered to aluminum jigs, using cyanoacrylate glue. The inner faces of the skin were adhered to each other with fibrin, 25-20 albumin, or 25-5 albumin. For the metal-metal tests, the inner faces of the aluminum jigs were adhered to each other with either fibrin or 25–20 albumin. The effective area of each face of the jig was 3 $cm^2$. The specimens were tested in axial shear, at a strain rate of 2.5 cm/min, to determine the adhesive shear strength.

For skin-skin specimens, the 25% albumin–20% PEG system had the highest shear strength value (about 5 times that of the fibrin glue system) while the 25-5 albumin system was 1.5 times as strong as the fibrin system (~6 kPa). For metal-metal specimens, the albumin glue (~35 kPa) was substantially stronger than fibrin (~1.5kPa) p<0.004). Therefore, the albumin glue provided greater adhesive strength to both aluminum and skin. This difference was accentuated in the metal-metal case. For the albumin glue, increasing the amount of PEG, used to crosslink the gel, significantly increased the adhesive strength. The use of albumin glue, therefore, may be a viable option for improving the stabilization and long-term success of dental implants.

EXAMPLE 20

Effect of Composition of an Adhesive Albumin Glue on Biocompatibility and Healing in an Incision Wound Model in Rabbits

METHODS AND MATERIALS

Materials

Albumin solutions were prepared by dissolving rabbit albumin (Sigma, St Louis, Mo.) in a 0.85% sodium chloride solution. PEG-SPA solution was prepared by solubilizing PEG-SPA (MW=20,000) in a basic HEPES solution. Specimens were prepared by combining 25 µL of each component. Fibrin was prepared by combining 25 µL each of human fibrinogen (Sigma, St Louis, Mo.) dissolved in distilled water, and bovine thrombin (Sigma, St Louis, Mo.) solubilized in a 40 mM calcium chloride solution. Wounds were treated as follows (2 wounds/treatment/animal): sutures (2/wound; control), fibrin glue, adhesive albumin (25% albumin solution, 15% modified PEG solution) (i.e., 25/15), adhesive albumin (25/10), and adhesive albumin (30/10).

Surgical Procedure

Eight New Zealand White rabbits were sedated with Ketamine and Xylazine, shaved, and cleaned with Betadine to prepare a sterile field. Rabbits were anesthetized using Isofluorane. Five full-thickness incisional wounds, 2.5 cm long, were created on each side of the spine. The epidermis and dermis were cut, with care taken to avoid cutting the underlying panniculous carnosus muscle. After blotting each wound to remove any blood, adhesive was applied (25 µL/solution). After glue was allowed to clot in wounds for 15 seconds, excess was squeezed out and each wound was held closed for one minute.

Evaluations

Wounds were visually examined daily and photographed every three or four days. Wound closure, defined as apposed skin with only a surface scab or no scab, was noted. At each of seven and fourteen days post-operatively, four rabbits were sacrificed. In four rabbits, all wounds were used for histology. From two of the seven-day rabbits, and two of the fourteen-day rabbits, only five of the ten wounds were used for histology, with the other wounds used for different analyses. Immediately post-sacrifice, strips approximately 6 mm×1 cm were excised for histological analysis and placed in 10% neutral buffered formalin.

Specimens were processed, embedded in paraffin, sectioned and placed on slides. To microscopically examine cellular response and the wound region, specimens were stained with hematoxylin and eosin. Digital images (4×, 20× and 40×magnifications) were obtained using a microscope (A×70, Olympus, Melville, N.Y.) and digital camera (OLY-750, Olympus, Melville, N.Y.). From the 4×images, the wound region, material remaining, and new tissue were traced using image analysis software (ImageProc Toolkit, Reindeer Productions, Raleigh, N.C.; Adobe Photoshop, Adobe Systems, Mountain View, Calif.). Material remaining and tissue infill were represented as volume fractions of the wound area, calculated by dividing the area of material remaining (or new tissue) by area of the wound region. Wound region was defined as the area originally created by the incisions (i.e., empty of tissue at time zero). Wound closure, as indicated by the presence of a continuous epidermis, was also noted. From the 20×images, volume fraction of blood vessels was measured. Percent of neutrophils, macrophages and fibroblasts (i.e., as a percent of the total of all three) was determined from the 40×images.

RESULTS

Wound Closure

Results from both the visual and microscopic analyses at seven and fourteen days were similar. In one rabbit, seven of the ten wounds did not close. By day one, three of the wounds appeared infected and were scrubbed and received a topical antibiotic. No wounds on this rabbit were closed at one week. After eliminating this rabbit, all wounds were closed by one week—as determined from histological specimens—except for two sutured wounds and two fibrin treated wounds. All wounds, excised at two weeks had closed. The resultant percent of closed wounds per treatments, as seen in histological specimens, shown in Table 1.

TABLE 1

| treatment | material remaining (%) | | tissue infill (%) | | closed epidermis (% wounds) | |
|---|---|---|---|---|---|---|
| | 1 week | 2 weeks | 1 week | 2 weeks | 1 week | 2 weeks |
| sutures | n/a | n/a | 87.3 ± 9.4 | 91.3 ± 5.2 | 66.7 | 100 |
| fibrin | 3.65 ± 6.32 | 0.04 ± 0.11 | 78.1 ± 7.6 | 95.2 ± 3.8 | 66.7 | 100 |
| 25/15 | 10.4 ± 4.49 | 2.14 ± 5.23 | 73.1 ± 10.0 | 89.7 ± 11.9 | 100 | 100 |
| 25/10 | 7.01 ± 7.94 | 1.83 ± 2.23 | 79.9 ± 10.3 | 92.6 ± 6.1 | 100 | 100 |
| 30/10 | 4.48 ± 4.39 | 0.00 | 84.0 ± 14.5 | 96.7 ± 2.8 | 100 | 100 |

Material Remaining

Figure 2:
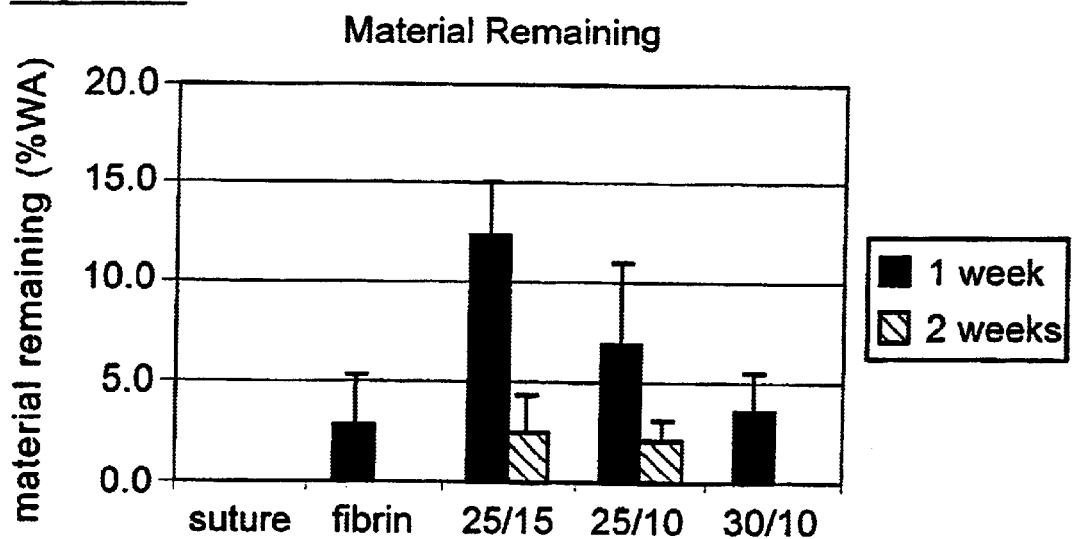
FIG. 2 is a histogram illustrating the percent of wound area filled with remaining material wherein bars represent standard mean error (SEM)

Fibrin and 30/10 adhesive albumin degraded fastest, at similar rates, with a mean of 3.6% and 3.4% material-remaining at one week, respectively. By two weeks; there was less than 0.5% of 30/10 albumin or fibrin remaining. Increasing PEG-crosslinker concentration slowed degradation at one week, with 12.3% material remaining in the 25/15 treated wound vs. 7.0% remaining in the 25/10 treated wound. At two weeks, a mean of 2.1% and 1.8% material remained in the 25/15/ and 25/10 closed wounds, respectively, as shown in FIG. 2.

Tissue Infill

In some specimens, there was a region devoid of any evident tissue ingrowth or material. In most cases, the open areas were surrounded by a slightly denser layer of cells, suggesting a capsule formation. This region may have been filled with fluid, or with tissue or material that was removed in the histological processing. For this reason, a tissue infill is presented separately from material remaining.

Figure 3:
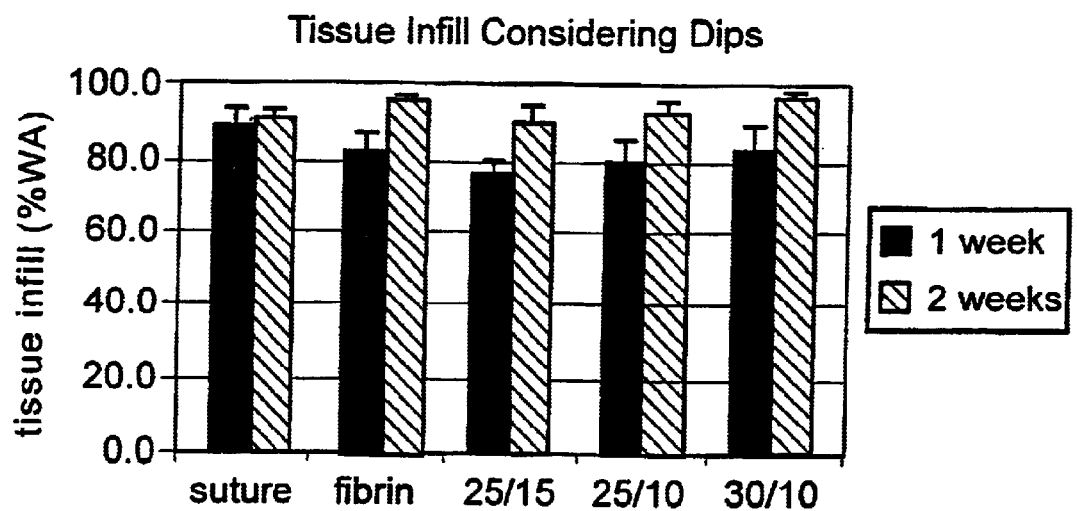
FIG. 3 is a histogram illustrating the percent wound filled with new tissue wherein bars represent standard mean error (SEM)

Referring to FIG. 3, by one week, wounds in all treatment groups were filled with at least 75% new tissue. The suture-closed wounds were filled 96.4±1.5%, on average. The 25/15 albumin treated wounds had the least infill at one week (mean 76.7±10.0%). Fibrin treated wounds showed an infill of 92.3±11.3% at one week, which was slightly less than that seen with the 10% PEG-SPA albumin materials (25/10 and 30/10), although none of the differences were significant. By two weeks, wounds were at least 90% filled, on average, with the sutured wounds possessing the least mean infill (89.7±9.1%). Wounds treated with the 25/15 albumin demonstrated a mean infill of 94.1±5.5%, similar to the fibrin treated wounds (94.2±3.4%). The 30/10 albumin treated wounds showed the most infill at two weeks, with an average 96.7±2.8% infill.

Many wounds demonstrated a slight "depression" at the surface. There was typically either albumin or scab material was present in this depressed area. At one week, this area was largest (mean 14.2±11.1% wound area) in fibrin treated wounds, and smallest in the 25/15 and 30/10 treated wounds (1.9±1.6% and 2.1±3.6% wound area, respectively). At two weeks, this region was largest in the suture treated wounds (6.5±3.5%), as opposed to the 25/10 and 25/15 albumin closed wounds (1.7±1.4% and 1.8±1.7% wound area, respectively).

Inflammatory Response

Figure 4A:
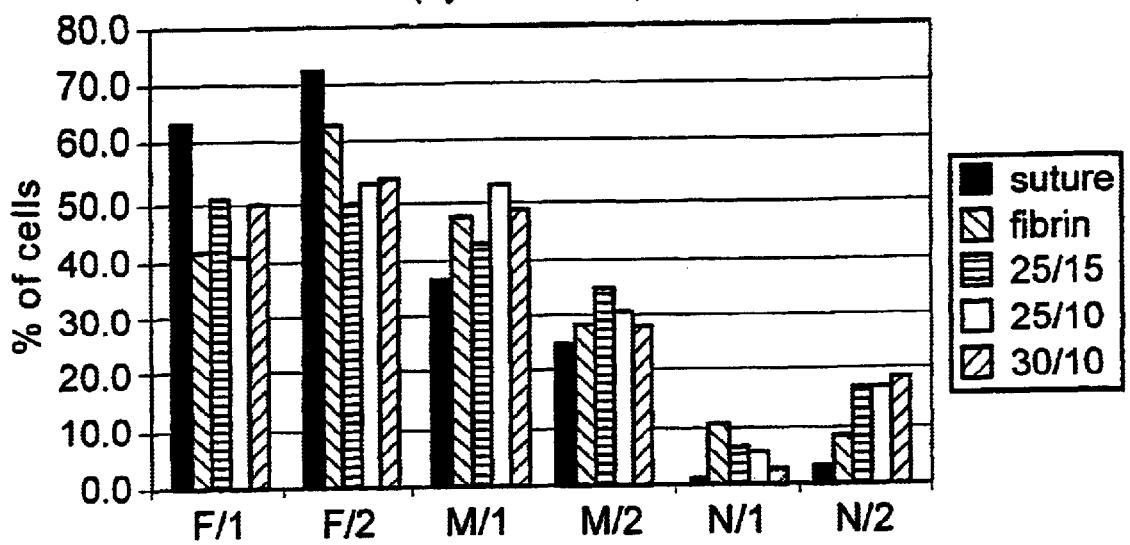
FIG. 4A is a histogram illustrating the percent inflammatory cells (of all cells in the wound region) by week wherein bars represent standard mean error (SEM)
Figure 4B:
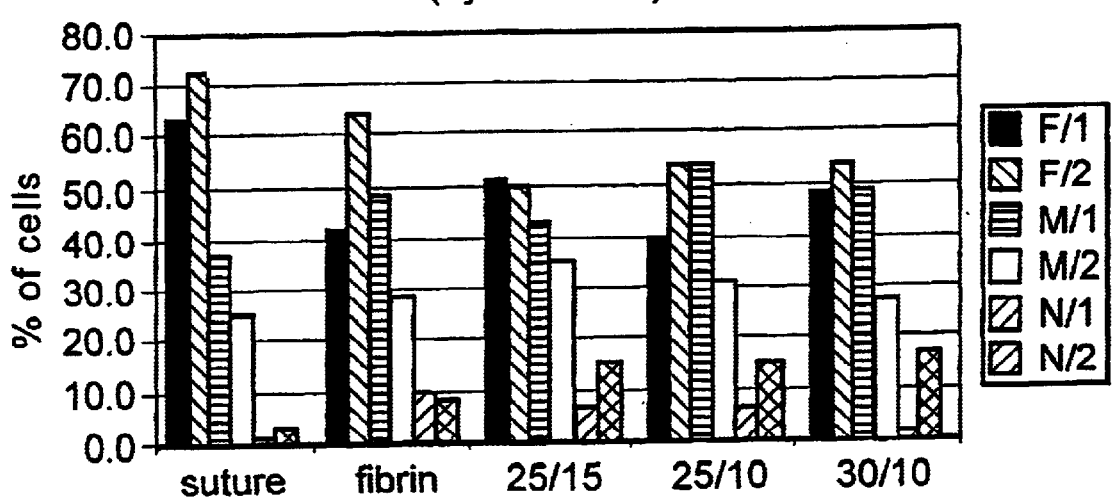
FIG. 4B is a histogram illustrating the percent inflammatory cells by material of all cells in the wound region wherein bars represent standard mean error (SEM)

Inflammatory cells in the wound region included neutrophils and macrophages. Other cells, including lymphocytes and giant cells, were seen in very small quantities in some wounds as shown in FIGS. 4A and 4B.

DISCUSSION

Wound Closure

By two weeks, all wounds had a complete epidermis, indicating that all treatments, including the control (sutures), are effective closure treatments. While epidermal closure is one measure of wound healing, it was evident from the histology that epidermal closure did not necessarily constitute complete material metabolism or tissue infill within the dermis.

Material Remaining

Use of a degradable material allows for replacement of the material by new tissue, resulting in complete tissue infill, constituting complete healing. A degradable material should degrade slow enough to remain present long enough to provide adequate structural support (e.g., as a mechanical structure or tissue scaffold), or to deliver a drug at an appropriate rate and duration, to facilitate optimal healing. It should also degrade fast enough to not interfere with new tissue growth.

For the albumin materials, the goal was to achieve material degradation and resolution of the inflammatory response faster, or at least as quick, as with fibrin. In the wounds treated with the albumin adhesive with the highest concentration (30%) of the natural component, albumin, the degradation rate was similar to that of fibrin. Slightly slower degradation was associated with the material with increased crosslinker content (i.e., 25/15 vs. 25/10).

Tissue Infill

Because it is not known whether or not the empty areas in some specimens were filled with fluid, cells or remaining adhesive, it is not possible to draw definitive conclusions about the subepidermal histology.

Inflammatory Response

While inflammatory response is required for normal wound healing, a prolonged inflammatory response may indicate a chronic pathological condition. The inflammatory response must be resolved before complete healing can occur. The inflammatory response observed here in the albumin treated wounds did not resolve as quickly as in the fibrin treated wounds. Based on rate of resolution between one and two weeks however, it is expected that the inflammatory response would be completely resolved by three weeks or before.

Blood Supply

In all wounds, blood supply, as measured by volume fraction of blood vessels, decreased between one and two weeks. At one week, volume fraction of blood vessels was highest in the 25/15 treated wounds (mean 50.9%) and lowest in the suture wounds (42.9%), with values in all albumin treated wounds higher than both the sutured and fibrin treated wounds. Between weeks one and two, mean blood vessel volume fraction decreased between 31–41% in all treatment groups except the 25/10 group, which decreased only 20%.

CONCLUSIONS

Although tissue infill was not complete at one or two weeks, epidermal closure occurred in all albumin treated wounds by one week, and in all wounds by two weeks. In both sutured and fibrin treated wounds, the epidermis of 33% of the wounds was not complete by one week. Tissue infill in both, however, was slightly higher in those wounds at one week. By two weeks, tissue infill in all wounds was over 90%. Of the albumin materials, highest infill was associated with a higher albumin concentration, suggesting that higher content of the natural component of the adhesive induced faster metabolization.

While some cells were present in the albumin adhesive, this occurrence was not common. Degraded areas around the cells suggest that the cells were metabolizing the material; In some instances, cells were present in material on the outside of the wound.

Wounds treated with albumin were more likely to have a smaller depression at the external surface of the wound, suggesting a smoother scar. The largest mean area of depression was associated with fibrin (14% wound area) at one week, and fibrin at two weeks (6% wound area).

EXAMPLE 21

Effect of Porosity on Shear Strength of an Albumin Adhesive

METHODS AND MATERIALS

Preparation of Materials

Adhesive albumin was prepared by combining an albumin solution and solubilized crosslinker polymer, 1:1 (v.v). Albumin solution was prepared by dissolving human albumin (Sigma, St Louis, Mo.) in a 0.85% sodium chloride solution. PEG-SPA crosslinker solution was prepared by solubilizing PEG-SPA (MW=20,000) (Shearwater Polymers, Huntsville, Ala.) in a basic HEPES solution.

Specimens were prepared by combining the two fluid components 1:1 (v/v).

For porous specimens, polyethylene glycol (PEG) particles (MW=100,000) (Sigma Chemical, St Louis, Mo.) were sprinkled on the adhesive layer after mixing the albumin and modified-PEG solutions. The polymer particles dissolve immediately, leaving a void. Particles were divided by size by sifting PEG particles through nylon meshes of known spacing. The "small" particles were separated out using 40 $\mu$m and 120 $\mu$m meshes, and the "large" particles sorted using. 120 $\mu$m and 200 $\mu$m meshes. To estimate particle volume of each pore size required for 10% and 20% porosity, densities of the two size ranges of particles were calculated by weighing 100 $\mu$L particles.

Examination of Structure

Both the particles and the structure of adhesive albumin clots obtained with different particle sizes were examined using light microscopy. For examination of the particles, particles were randomly sprinkled onto a glass slide. One to three images of the particles were digitized at 10×magnification (Provis A×70, Olympus, Melville, N.Y.) to provide for a minimum of 30 and 50 samples of small and large particles, respectively. Particles were traced using image analysis software (Adobe Photoshop, Adobe Systems, Mountain View, Calif.; ImageProc Toolkit, Reindeer Productions, Raleigh, N.C.) to obtain particle area. Approximate diameter was calculated from the area value of each particle. A mean diameter value was calculated for the small and large particles.

Clot specimens (30 $\mu$L spread over 1 cm$^2$) with small or large pores were created on glass slides, and examined at 10×magnification. Again, images were digitized and pores traced using image analysis software. Each pore was traced, area measured, and values calculated, as for the particles. Three sample groups of small pores and five sample groups of larger pores were traced to provide a minimum of 50 and 30 samples, respectively.

Evaluation of Shear Strength

Figure 5:
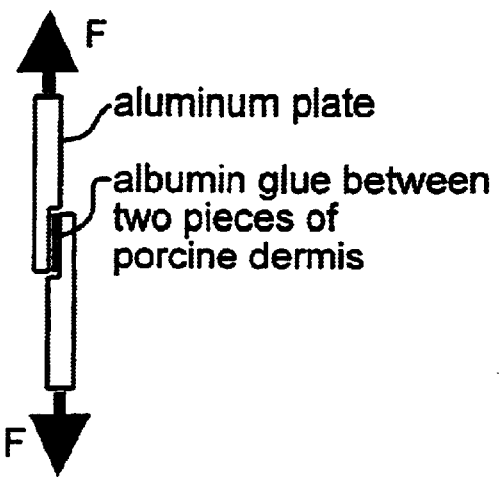
FIG. 5 is a diagrammatical illustration of the test set-up for evaluating shear strength of various adhesives.

Porcine dermis (Brennen Medical Inc, St Paul, Minn.) (6.25 cm$^2$.) was glued, hair side down, to aluminum jigs using cyanoacrylate glue as shown in FIG. 5. The glued skin pieces, kept moist by a covering of saline-soaked gauze, were allowed to set for fifteen-thirty minutes. After the moist gauze was removed and the skin pieces were blotted with dry gauze, albumin solution and modified-PEG solution were applied to one piece of skin and mixed with one applicator tip. Adhesive albumin with four different porosity configurations was tested: no pores; 10% volume porosity, small pores (10/small); 20% volume porosity, small pores (20/small); and 20% volume porosity, larger pores (20/large). For each specimen, a total of 188 $\mu$L volume of material was applied between the pieces of skin, for an approximately 300 $\mu$m layer of adhesive.

Following application of each test material, specimen pairs were pressed together and allowed to set for one hour, with a 240 g weight applied across five specimens to allow for even setting. After setting, specimens were clamped (Quick-Grip Micro Bar Clamp and Spreader, American Tool Companies, USA) to prevent specimen damage during loading, and loaded into custom prepared fixtures in an MTS Minn Bionix 858 System (MTS Systems, Eden Prairie, Minn.) After clamp removal, specimens were tested in shear at 2.5 cm/minute until failure. Load and deformation were recorded. Three runs were performed, with five specimens per sample type tested in each run.

Figure 6A:
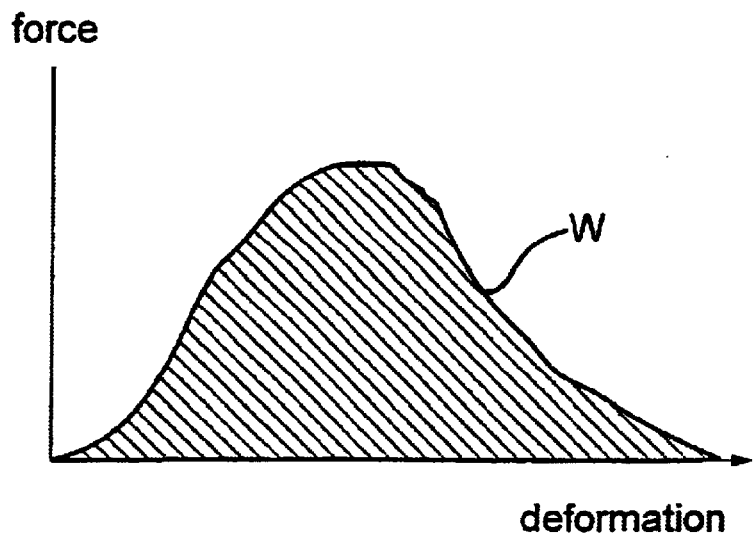
FIG. 6A is a force-deformation plot wherein the area under the plot was considered for calculation of failure energy (W) from force-deformation curve.
Figure 6B:
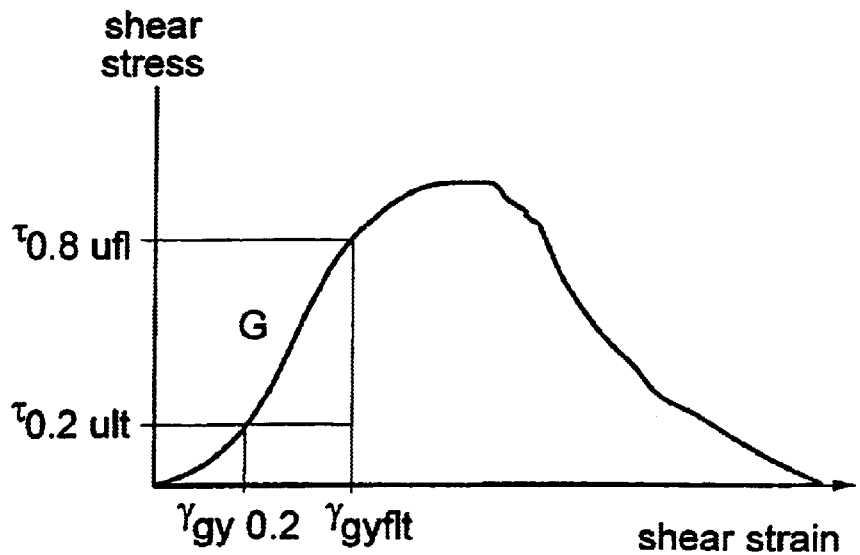
FIG. 6B is a plot wherein the shear modulus (G) is calculated from a stress-strain curve.

Force-deformation plots and stress-strain plots were generated and are shown in FIGS. 6A–B. Values were calculated as follows:

$\tau_{ult}$=ultimate shear strength=$F_{max}/A$ $\gamma_{xy}$=shear strain=tan $(dy/x) \approx dy/x$ $G$=shear modulus=$(\tau_{0.8\ ult}-\tau_{0.2\ ult})/(\gamma_{xy\ 0.8}-\gamma_{xy\ 0.2})$ $W$=failure energy=$\int F\ dy$ Where
$F_{max}$ = maximum attained load
A = bonded area of skin = 6.25 cm$^2$
dy = deformation (in direction of load)
x = material thickness
   $\approx$ volume adhesive applied/A = 300 $\mu$m Standard statistical values, including mean, standard deviation and standard mean error ($\pm 1$) were calculated. ANOVA analyses with Fisher's protected least significant difference test were performed (p<0.05). To determine the failure mode of the adhesive materials, specimens were visually examined after testing to identify distribution of the materials. Because it was suspected that humidity and temperature may affect material shear strength, each was recorded each day of testing.

RESULTS

Examination of Structure

Figure 7A:
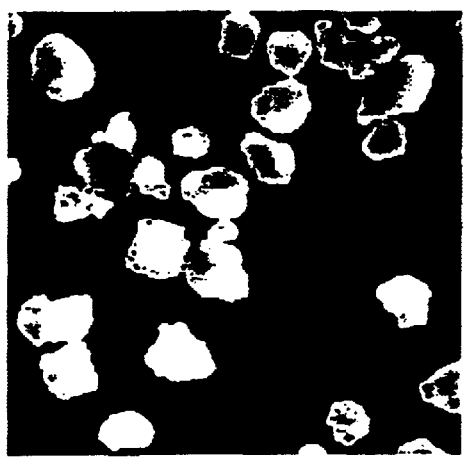
FIG. 7A illustrates polyethylene glycol particles with an average diameter ranging between 10–120 $\mu$m, MW=100,000.
Figure 7B:
FIG. 7B illustrates polyethylene glycol particles having an average diameter between 120–200 $\mu$m, MW=100,000.

For both the small and large particles, mean particle size was approximately equal to the theoretical average particle size, calculated as the median of the particle size range. Theoretical median diameter of the small (40–120 $\mu$m diameter, FIG. 7A) and large particles (120–200 $\mu$m diameter, FIG. 7B) was 80 $\mu$m and 160 $\mu$m, respectively. Mean of the, small particle samples (n=51) was 79±16 $\mu$m. Mean of the large particles (n=31) was 160±40 $\mu$m.

Figure 8A:
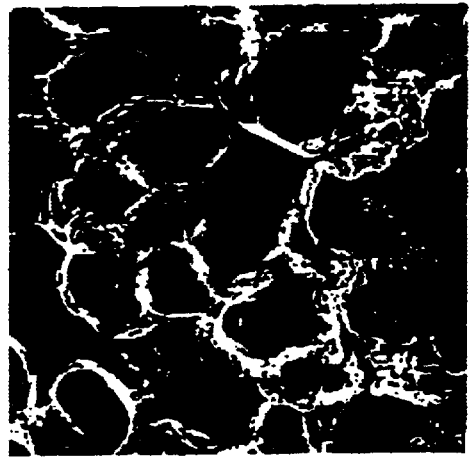
FIG. 8A illustrates the resultant clots formed when particles are added to adhesive with 40–120 $\mu$m average diameter particles added.
Figure 8B:
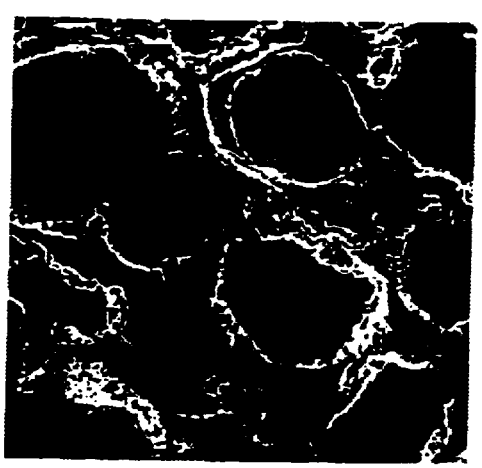
FIG. 8B illustrates the resultant clots formed when particles added to the adhesive having 120–200 $\mu$m average diameter particles were added.

In specimens prepared with small particles, mean pore size was 97±28 $\mu$m diameter (n=62). In specimens prepared with large particles, pores were 193±57 $\mu$m diameter (n=37). The range of pore sizes was 48–181 $\mu$m, and 105–363 $\mu$m, in the small and large pore clots, respectively. Resultant mean pore size, as observed with light microscopy, was approximately 23% and 21% larger than mean particle size, for small and large particles, respectively. See FIGS. 8A and 8B.

Evaluation of Shear Strength

Figure 9:
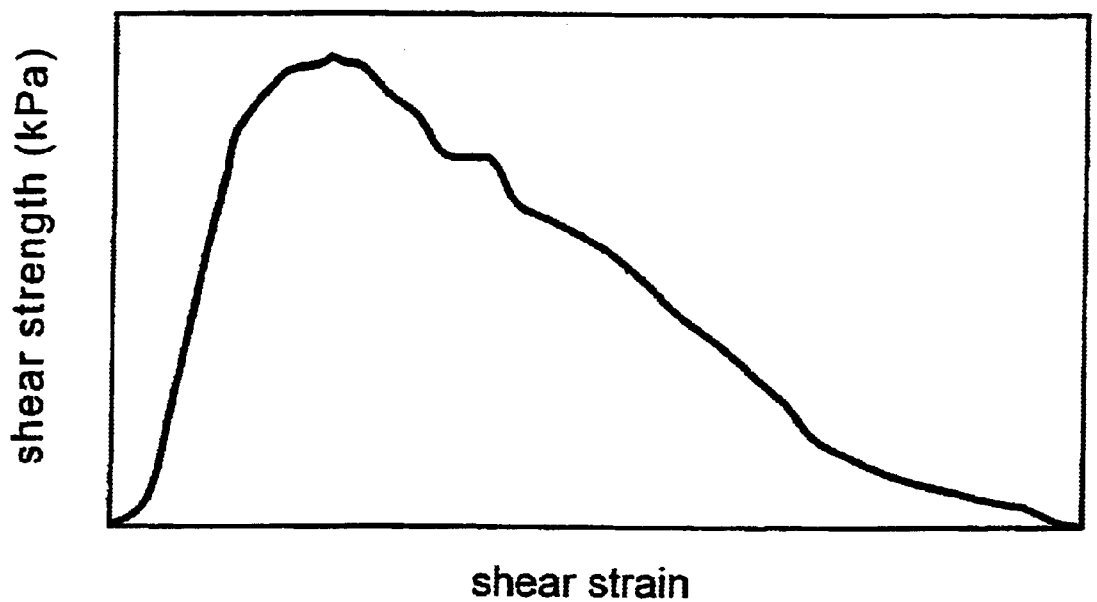
FIG. 9 is a graph illustrating a stress-strain curve.

Data from individual runs was pooled for analysis. Data from each individual run was also examined and it was confirmed that trends seen within each run were similar to those in the pooled data. Of the fifteen specimens tested per sample type, between one and three specimen results were eliminated from analysis due to damage during testing. Specimen results were eliminated for the following reasons: peeling of skin from metal jig; visible motion in the glue joint during loading into the fixture; jamming of the test jig during loading; or, visible evidence of accumulation of adhesive or sticking of adhesive at the end(s) of a specimen. Up to an additional two results from each sample group were eliminated as outliers per the boxplot rule (Devore, Probability and Statistics, 4$^{th}$ Ed., Boston, Duxbury Press). Stress-strain curves were typically slightly asymmetric, with the ascending slope steeper than the descending slope (see FIG. 9).

As expected, shear strength of the nonporous adhesive albumin (10.83±4.92 kPa) was stronger (28–35%) than the porous materials (Table 2), although the difference between the non-porous and porous materials was significant (p<0.05) only for the 90/small material. There were no significant differences in ultimate shear strength between the three porous materials.

TABLE 2

| material | n | $\tau_{ult}$ ultimate shear strength (kPa) | $\gamma$ strain at ultimate strength | W failure energy (J) | G shear modulus (kPa) |
| --- | --- | --- | --- | --- | --- |
| no pores | 10 | 10.83 ± 4.92 | 3.47 ± 0.78 | 10.41 ± 4.72 | 9.57 ± 6.20 |
| 10/small | 14 | 8.05 ± 2.59 | 2.19 ± 0.66 | 6.04 ± 1.84 | 14.73 ± 4.56 |
| 20/small | 13 | 8.40 ± 2.79 | 1.78 ± 0.67 | 5.89 ± 2.26 | 15.54 ± 4.31 |
| 20/large | 10 | 8.17 ± 1.75 | 2.31 ± 0.75 | 5.77 ± 0.72 | 18.02 ± 7.24 |

Strain at ultimate strength was significantly higher for the nonporous adhesive (3.47±0.78 kPa) than for the porous materials (see FIG. 10). While these differences in tolerated shear strain of the porous materials were not significant, the 20/small pore material tolerated the least (1.78±0.67 kPa).

With the testing method used, variation in the slope of the stress-strain curve, or the shear modulus, was large. Despite this, shear modulus of the material with no pores (9.57±6.20 kPa) was significantly lower than that of the porous materials (p<0.03).

Temperature and humidity varied only slightly on the test days, with temperature and humidity values in the lab of 72–76° F. and 42–47%, respectively. Results varied slightly from run to run, but did not correlate with temperature or humidity differences.

Visual examination revealed that material remained on both pieces of skin of each sample pair, and that, except for isolated patches in the material layer on a few specimens, remaining material covered a majority of each skin piece. This distribution suggested cohesive, rather than adhesive failure, since the failure appears to have occurred within the layer of adhesive rather than at the interface between the glue and substrate.

DISCUSSION

In previous studies of porous vs. non-porous fibrin adhesive to secure skin grafts in rabbits, it was found that porosity was associated with increased graft removal (Osborne et al. (1996) Trans. Soc. Biomatls. I:27). There was a 30% decrease in shear strength when pores were formed at a 12% volume, using particles 170–240 μm diameter. Pores in fibrin clots were associated with failure of 40% of grafts at both three and ten days in grafted wounds in rabbits, although only 20% of porous fibrin grafts failed at ten days when acidic fibroblast growth factor (FGF-1) was included in the clots (Osborne et al. (1996) Trans. Soc. Biomatls. I:27).

This was a primary motivator for this study. By better understanding and anticipation of the reduction in strength associated with changes in porosity, materials may be developed to better preserve strength. Selection of PEG-derivative crosslinked adhesive albumins, which have been observed by some to possess superior adhesive compared to fibrin (Truong et al. (1996) Trans. Soc. Biomatls. II-73; Barrows et al. (1996) Trans. Soc. Biomatls. I-8; Huang et al. (1997) Trans. Wound Healing Soc. 7:63), was intended to compensate for some of the reduction in strength by providing a stronger material to start with. Even without induced macropores, fibrin has been found by some to have insufficient strength for some applications (Gibble et al. (1990) Tarnsfus. 30(8):741–47; Truong et al. (1996) Trans. Soc. Biomatls. II-73).

Loss of grafts may lead to additional surgery and prolongation of healing. Additional surgery implies added cost, extended hospital stay, and requirement of additional skin for grafting. If insufficient skin is available from the patient, this may require waiting for previously used donor sites to heal. Prolonging time to coverage and healing of wounds may also result in increased chance of infection.

As previously eluded to, while adequate adhesion is a primary concern, so too is sufficient penetrability of the material to ensure that cells can move in and replace the material easily. While this can be accomplished by inclusion of pores, this can also be achieved by providing a material that degrades in synchronization with the rate of new tissue growth. In most degradable materials, this rate of degradation can be increased by increasing material surface area, such as with pores. Thus, incorporation of pores in a degradable material not only better facilitates immediate passage through the material, but also can be used to adjust the degradation rate.

Examination of Structure

Two different pore size ranges were selected, to determine the effect of size on material strength. To ensure tissue ingrowth into material placed in a wound, pores should be at least 40–50 μm in diameter (Feldman et al. (1983) Biomatls. 4(2):105–111; Morehead et al. (1994) Otolaryng. Clin. North Am. 195–201) and optimally 100 μm (Dagalakis et al. (1980) J. Biomed. Mater. Res. 14:511–528). Also, bacteria can grow into pores greater than 1 μm, but phagocytic cells needed to clear away bacteria cannot penetrate pores smaller than 50 μm (Morehead et al. (1994) Otolaryng. Clin. North Am. 195–201). Therefore very small pores, such as those in unmodified fibrin (i.e., less than 10 μm) (Blomback et al. (1990) Fibrinogen, Thrombosis, Coagulation, and Fibrinolysis, NY: Plenum Press); do not allow ingrowth and are more likely to harbor infection (Morehead et al. (1994) Otolaryng. Clin. North Am. 195–201).

The ideal pore size in materials placed on wounds is not known. Theoretically, expanding pore size may increase tissue ingrowth by widening the pathway for new tissue. On the other hand, this may also increase degradation rate by expanding the amount of material surface area and may decrease shear strength by reducing contact area between the material and substrate.

The particle sizes used were selected to produce pores approximately between 50 and 200 μm, with median values equally spaced within that range, assuming that mean diameter would be similar to the median, and that pore size would approximately correspond to particle size. Mean small and large particle size, measured from light microscopy images, corresponded well with the median values of each particle range. Pore sizes associated with each particle size range were approximately 25% larger than mean particle size, suggesting a slight expansion in the void associated with dissolution of the particle. Standard deviation of pore size (29–30%) was only slightly larger than that of particle size, implying that the distribution is similar.

One disadvantage of the methods of pore examination used here is the lack of a cross-sectional view. Future studies may involve examination of the matrices using confocal microscopy. Without this distribution, it is not possible to conclude that pores are, interconnecting and it is likely that they are not. Design of the material, however, is based on the premise that the material is degradable. It is assumed that thin interstices between pores will degrade in a short amount of time, allowing for passage of cells, chemicals and new vascular and collagenous tissue.

Evaluation of Shear Strength

As expected, inclusion of pores into the material reduced ultimate shear strength (significance at p<0.08). Differences between the three porous materials were slight, however. Shear strain and failure energy of the nonporous material was significantly higher (p<0.001) than that of the porous materials, which reduced shear strain by 37, 49 and 33% (10/small, 20/small and 20/large, respectively). These results suggest that shear strain of a 20% porous material can be improved either by increasing pore size or decreasing pore volume.

Shear modulus (i.e., slope of the elastic region of the stress-strain curve) of the nonporous material was significantly lower (p<0.03) than that of the porous materials (35–47% lower). This difference may be, in part, due to the effective reduction in contact area between the material component of the matrix and the substrate, with the inclusion of pores. The area of the pores at the substrate was not considered in calculation of the strength or other values since our interest was in the properties of the resultant scaffolds. Again, differences between the porous materials were only slight.

Differences among the porous matrices were most pronounced for shear strain and shear modulus. Material with 20% porosity/small pores (i.e., 20/small) showed lower shear strain than both the lower porosity (10/small) and the larger pore (20/large) materials. These results suggest that shear strain can be improved either by increasing pore size or by decreasing pore volume. A high shear strain is desired because it reflects how much the material can deform before it breaks. While high shear strength is required to protect material from failure with high shear forces, high shear strain at ultimate strength can aid in resistance to failure from small shear forces acting on the grafts, such as with slight patient movement or healthcare worker handling.

There are theoretical structural implications associated with changing either porosity or pore size. Using the mean diameters for small and large pores measured from light microscopy images, and approximating each pore as a sphere, surface area of the pores within a material can be calculated, for a given pore volume ($V_{matrix}$) (e.g., 188 μL). Surface area (SA) can be calculated as $SA = N \times SA_{single\ pore}$, where N=number of pores=$V_{all\ pores}/V_{single\ pore}$. For this study, $V_{all\ pores}$ is equal to either $0.1 V_{matrix}$ or $0.2 V_{matrix}$ (10 or 20% porosity, respectively). This increase in surface area translates to an increase in length and/or decrease in thickness of interstices.

Assuming the same volume of porosity (e.g., 20%), theoretical total surface area (SA) in a matrix with small pores is approximately 1.97 times as great as that with large pores, (i.e., $SA_{small}:SA_{large}=1.97:1$). Assuming one uniform pore size, as the volume of porosity is increased from 10% to 20%, the corresponding theoretical surface area of the pores is doubled (i.e. $SA_{20}:SA_{10}=2:1$).

These theoretical surface area differences, which imply a change in length of interstices, do not directly correlate with results obtained here. Expansion of the interstices between pores implies that given some degree of material elasticity—the matrix should tolerate more deformation. As previously mentioned, however, this increase in void volume and area results in reduced material (i.e., as opposed to void space) at the surfaces subject to the load. In the porous scaffolds, larger pores resulted in higher shear strain (i.e., 20/large vs. 20/small). This shear strain was similar to that of the 10/small scaffold. The fact that the highest shear strain was obtained with the nonporous material indicates that inclusion of the pores weakened the scaffold too much to overcome failure with increased deformability.

The PEG-SPA crosslinked albumin adhesive used here was a slightly different composition than that previously studied by Huang and associates (Huang et al. (1997) *Trans. Wound Healing Soc.* 7:63) in earlier shear strength tests. With a 25% albumin-20% PEG-SPA (i.e., 25/20) system on skin, shear strength was approximately five times stronger than that of the fibrin glue (75–90 mg/mL fibrinogen, 500 U/mL thrombin). Shear strength of the 25/5 system on skin was approximately 1.5 times stronger than that of the fibrin system. The composition selected for use here was based on degradation and biocompatibility, in addition to strength, as seen in a study of the material in incisional wounds in rabbits. The subsequent selection of a composition of 30% albumin/10% PEG-SPA was based on degradation properties and resolution of inflammatory response. All materials studied resulted in wound closure. The 30/10 material possesses slightly lower shear strength than the 25/15 system, for example, as well as compared to the 25/20 system used by Huang and coworkers. On the other hand, it exhibited higher shear strain at ultimate strength and approximately equal failure energy, compared to the 25/15 material, suggesting similar toughness. This material was selected for its degradability rate similar to fibrin, and superior shear strain at ultimate strength. Although ultimate strength is lower than for the 25/15 material, higher shear strain, with similar failure energy, suggests that the material tolerates more motion before failing.

CONCLUSIONS

In a PEG-SPA crosslinked albumin adhesive, with particles added to create pores, shear properties can be modified by changing particle size and particle volume added. Mean pore diameter was approximately 25% greater than the diameter of particles used to create the pores. Incorporation of three different configurations of pores reduced the shear strength by approximately 25% (i.e., 22–26%). Failure energy was reduced by approximately 45% (i.e., 42–45%). There were no significant differences in any values for the porous materials. Shear strain was reduced slightly both by increasing porosity with a given pore size, or by decreasing pore size for a given pore volume. Increasing pore size resulted in a slight increase in shear modulus, for a given volume. If initial strength can be improved, this system may show promise for application as a tissue adhesive to stabilize skin grafts.

Throughout this application, various publications are referenced by citation and number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of the description rather than of limitation.

Obviously, many modifications and variations of the present invention are possible in light of the above teachings. Therefore, it is to be understood that within the scope of the appended claims, the invention may be practiced otherwise than as specifically described.

In view of the teaching presented herein, other modifications and variations of the present inventions will be readily apparent to those of skill in the art. The foregoing drawings, discussion, and description are illustrative of some embodiments of the present invention, but are not meant to be limitations on the practice thereof. It is the following claims, including all equivalents, which define the scope of the invention.

REFERENCES

ALBREKSTSSON et al. (1982) Ultrastructural analysis of the interface zone of titanium and gold implants. In: *Clinical Applications of Biomaterials*. Vol 4 (A. J. C. Lee, T. Albrektsson, and P. I. Branemark, eds), New York: John Wiley & Sons, pp. 167–177.

BARROWS et al. (1996) Evaluation of a new tissue sealant material: Serum albumin crosslinked in vivo with polyethylene glycol. *Trans. Soc. Biomatls*. I-8.

BLOMBACK et al. (1990) Native fibrin gel networks and factors influencing their formation in health and disease. (C. Y. Liu and S. Chen, eds), *Fibrinogen, Thrombosis, Coagulation, and Fibrinolysis*, New York: Plenum Press, pp. 1–23.

BLUM et al. Effect of Composition of an Adhesive Albumin Glue on Biocompatibility and Healing in an Incisional Wound Model in Rabbits.

BLUM et al. Effect of Porosity on Shear Strength of an Albumin Adhesive.

CRANIN et al. (1996) 9.4. Dental Implantation. In: *Biomaterials Science* (B. D. Ratner, A. S. Hoffman, F. J. Schoen, J. E. Lemons, eds), San Diego: Academic Press, pp. 426–435.

DAGALAKIS, et al. (1980) Design of an artificial skin. III. Control of pore structure. *J. Biomed. Mater. Res.* 14:511–528.

DEVORE J. L. Probability and Statistics, $4^{th}$ Edition. Boston: Duxbury Press;

FELDMAN et al. (1983) Electron microscopic investigation of soft tissue ingrowth into Dacron velour with dogs. *Biomatls* 4(2):105–111.

FELDMAN and von RECUM (1985) Non-epidermally induced failure modes of percutaneous devices. *Biomaterials*, 6(5)352–356.

GIBBLE et al. (1990) Fibrin glue: the perfect operative sealant? *Transfus*. 30(8): 74147.

HUANG et al. (1997) A comparison of the shear strength of fibrin and albumin glues. *Trans. Wound Healing Soc.* 7:63.

KILPADI et al. (1998) A comparison of the adhesive strength of albumin and fibrin glues for use with metallic implants. *Proc. of the 24th Annual Meeting of the Society for Biomaterials*, San Diego; Calif.

KILPADI et al. (1997) A comparison of the shear strength of fibrin and albumin glues. Seventh Annual Meeting of the Wound Healing Society, Nashville, Tenn.

MIKOS, et al., (1993)

MOREHEAD et al. (1994) Soft-tissue response to synthetic biomaterials. *Otolaryng. Clin. North Am.* 195–201.

MUSTOE et al. (1991)

NEUFELD et al., (1980)

OSBORNE et al. (1996) The effect of acidic fibroblast growth factor (FGF-1) delivered through a porous fibrin scaffold on meshed skin grafts. *Trans. Soc. Biomatls*. I:27.

PANDIT et al. (1994)

RIZZINO et al. (1988)

TRUONG et al. (1996) In vitro analysis of mechanical properties of a new tissue sealant material: Polyethylene glycol crosslinked serum albumin. *Trans. Soc. Biomatls*. II-73.

What is claimed is:

1. A bioadhesive scaffold material, said material comprising:

albumin;

a polyethylene glycol crosslinking agent;

10 to 50 volume percent of 10 to 500 micron polymeric beads imparting porosity, said beads selected from the group consisting of: polyethylene glycol and poly (ethylene oxide); and a modifying agent incorporated into said bioadhesive material, wherein said modifying agent is selected from the group consisting of: a tissue growth promoting agent fibroblast growth factor I (FGF-I), an anti-inflammatory and an antibiotic.

2. A bioadhesive scaffold material according to claim 1, wherein said polyethylene glycol comprises a modified polyethylene glycol.

3. A bioadhesive scaffold material according to claim 1, wherein said modifying agent incorporated into said bioadhesive material is said tissue growth promoting agent.

4. A bioadhesive scaffold material according to claim 3, wherein said tissue growth promoting agent is said fibroblast growth factor I, (FGF-I).

5. A bioadhesive scaffold material according to claim 1, wherein said modifying agent is said anti-inflammatory.

6. A bioadhesive scaffold material according to claim 1, wherein said modifying agent is said antibiotic.

7. A bioadhesive scaffold material according to claim 1, wherein the concentration of said albumin in said bioadhesive scaffold material ranges from approximately 0.1% to 50%.

8. A bioadhesive scaffold material according to claim 7, wherein said amount of said albumin in said bioadhesive scaffold material ranges from approximately 1.0% to 30% by weight.

9. A bioadhesive scaffold material according to claim 7, wherein said concentration of said albumin in said bioadhesive scaffold material ranges from approximately 10% to 30%.

10. A bioadhesive scaffold material according to claim 1, wherein said concentration of said polyethylene glycol crosslinking agent in said bioadhesive scaffold material ranges from approximately 0.1% to 30%.

11. A bioadhesive scaffold material according to claim 10, wherein said concentration of said polyethylene glycol crosslinking agent in said bioadhesive scaffold material ranges from approximately 5.0% to 25%.

12. A method for adhering tissue comprising the steps of applying and bonding bioadhesive scaffold material of claim 1 to the tissue.

13. A bioadhesive scaffold material according to claim 1 wherein said porosity imparting polymeric beads comprise polyethylene glycol.

14. A bioadhesive scaffold material according to claim 1 wherein said porosity imparting polymeric beads comprise poly(ethylene oxide).

15. A bioadhesive scaffold material according to claim 1 wherein said porosity imputing polymeric beads have a mean size ranging from 10 microns to 500 microns.

16. A bioadhesive scaffold material according to claim 15 wherein said porosity imparting polymeric beads have a mean size of from 120 microns to 200 microns.

* * * * *